(12) United States Patent
Wright, Jr. et al.

(10) Patent No.: US 6,476,290 B1
(45) Date of Patent: Nov. 5, 2002

(54) TRANSGENIC TILAPIA COMPRISING A HUMANIZED INSULIN GENE

(75) Inventors: James R. Wright, Jr., Halifax; Bill Pohajdak, Dartmouth, both of (CA)

(73) Assignee: Dalhousie University, Nova Scotia (CA)

( * ) Notice: Subject to any disclaimer, the term of this patent is extended or adjusted under 35 U.S.C. 154(b) by 0 days.

(21) Appl. No.: 09/484,848

(22) Filed: Jan. 18, 2000

Related U.S. Application Data

(63) Continuation-in-part of application No. 08/750,391, filed as application No. PCT/CA96/00171 on Mar. 22, 1996, now Pat. No. 6,015,713, said application No. 09/484,848, is a continuation of application No. 08/416,866, filed on Apr. 19, 1995, now Pat. No. 5,588,708.

(51) Int. Cl.$^7$ ...................... A01K 67/00; A01K 67/033; A01K 67/027; C12N 5/00

(52) U.S. Cl. ................ 800/20; 800/4; 800/13; 435/325

(58) Field of Search ............................ 800/4, 8, 13, 20; 435/325

(56) References Cited

U.S. PATENT DOCUMENTS 6,015,713 A * 1/2000 Wright, Jr. et al. ......... 435/378

OTHER PUBLICATIONS

RJ Wall et al., J Dairy Sci, "Transgenic Dairy Cattle:Genetic Engineering on a Large Scale," 1997, 80:2213–2224.*
RE Hammer et al., J Anim. Sci., "Genetic Engineering of Mammalian Embryos," Jul. 1986, 63:269–278.*
LJ Mullins et al., J. Clin. Invest., "Perspectives Series: Molecular Medicine in Genetically Engineered Animals, "Apr. 1996, vol. 97, No. 7, pp. 1557–1560.*
LM Houdebine et al., Experientia, "Transgenesis in fish," 1991,47, pp. 891–897.*
J de la Fuente et al., Genetic Analysis: Biomolecular Engineering, "Growth regulation and enhancement in tilapia: basic research finding and their applications," 1999, 15, 85–90.
Tl Pitkanen et al., Genetic Analysis: Biomolecular Engineering, "Transfer of growth hormone (GH) transgenes into Artic charr (*Salvelinus alpinus L.*) I. growth response to various GH constructs," 1999, 15, 91–98.
MGomez–Chiarri et al., Genetic Analysis: Biomolecular Engineering, "Evaluation of eukaryotic promoters for the construction of DNA vaccines for aquaculture," 1999, 15, 121–124.
MA Rahman et al., Transgenic Research, "Copy number related transgene expression and mosaic somatic expression in hemizygous and homozygous transgenic tilapia (*Oreochromis niloticus*)," 2000, 9:417–427.

* cited by examiner

*Primary Examiner*—Deborah Crouch
*Assistant Examiner*—Joseph Woitach
(74) *Attorney, Agent, or Firm*—Foley & Lardner; Stephen E. Reiter

(57) ABSTRACT

In accordance with the present invention, there are provided humanized fish insulin genes. Humanized insulin the present invention encode human insulin alpha and/or beta chains while using fish-preferred codons and regulatory sequences. These humanized genes are thus expressible in fish islet cells. Also provided are transgenic fish having islet cells containing and capable of expressing humanized insulin genes. These islet cells (Brockmann Bodies) can be xenotransplanted into subjects having diabetes. In this manner normoglycemia can be achieved in the recipient of the islets.

4 Claims, 6 Drawing Sheets

Insulin A-Chain

Gly-Ile-Val-Glu-Glu-Cys-Cys-His-Lys-Pro$^{10}$-Cys-Thr-Ile-Phe-Asp-Leu-Gln-Asn-Tyr-Cys$^{20}$-Asn

Insulin B-Chain

Val-Gly-Gly-Pro-Gln-His-Leu-Cys-Gly-Ser$^{10}$-His-Leu-Val-Asp-Ala-Leu-Tyr-Leu-Val-Cys$^{20}$-Gly-Asp-Arg-Gly-Phe-Phe-Tyr-Asn-Pro-Arg$^{30}$

FIG. 1

Insulin A-Chain

| | | | | | |
|---|---|---|---|---|---|
| Tilapia | GIVEE | CCHKP | CTIFD | LQNYC | N |
| Human | ----Q | --TSI | -SLYQ | -E--- | - |

Insulin B-Chain

| | | | | | | |
|---|---|---|---|---|---|---|
| Tilapia | VGGPQ | HLCGS | HLVDA | LYLVC | GDRGF | FYNPR |
| Human | FVN- | ----- | ---E- | ----- | -E--- | --T-K T |

FIG. 2

```
GAATTTACATCGATTGTGCAGTTTTGACAGAAAATGTTTTTATAGTTTGATTGTGGGGTGACAGCGGCTCTGGTTTCTGGTTCATTGGTGGA    100
GCAGATGC
CTTAAATGTAGCTAACACGTCAAAACTGTCTTTTACAAAAATATCAAACTAACACCCCACTGTCGGCGAGACCAAAGACCAAGTAACCACCT
CGTCTACG

AGATGAGAAAACACAAAGTTGTCTGAAACACGCGTCCTCCTTCGTCATGGACAGCTCGTCATGGTAACGCTCTTTCTCGGTCAGTTGTGCAG    200
CTTCTTTA
TCTACTCTTTTGTGTTTCAACAGACTTTGTGCGCAGGAGGAAGCAGTACCTGTCGAGCAGTACCATTGCGAGAAAGAGCCAGTCAACACGTC
GAAGAAAT

AGAGACTAACAAGCTGGAACAAGAGCTCTGTCAGCACACCTCTGACACCCATTAAGCACTCTTTGGATGGCAGATGGTTTGATGAGGCTCTG    300
GGTTTTTG
TCTCTGATTGTTCGACCTTGTTCTCGAGACAGTCGTGTGGAGACTGTGGGTAATTCGTGAGAAACCTACCGTCTACCAAACTACTCCGAGAC
CAAAAAC

TGCAGTCGGGCTCTTTCTCACTGCGTGACTGAAAAAATACAAACTTGAACTAGAGCTGAAGTCATCTTAGACCCATAACTACAATAAACTAT    400
TTGTAACA
ACGTCAGCCCGAGAAAGAGTGACGCACTGACTTTTTTATGTTTGAACTTGATCTCGACTTCAGTAGAATCTGGGTATTGATGTTATTTGATA
AACATTGT

TCAGGACAGTCAAGCTTTTGTCTTTGTGTTTCATGCTGTCTGCGTAGTTCAGGGTTGTCAAACATCAGGCCCGGGGGCCGAGAAATTGGCCA    500
CCAAACAC
AGTCCTGTCAGTTCGAAAACAGAAACACAAAGTACGACAGACGCATCAAGTCCCAACAAGTTTGTAGTCCGGGCCCCCGGCTCTTTAACCGG
TGGTTTCTG

TCTAAGCCACCTCATTGAATGACTTTGAACAATGTGATGAAGGGCATGAGTTTTAAACTTCATATTCATGAGTTTTACAGTTTTCCAGCTGA    600
TAAAGAA
AGATTCGGTGGAGTAACTTACTGAAACTTGTTACACTACTTCCCGTACTCAAAATTTGAAGTATAAGTACTCAAAATGTCAAAAAGGTCGAC
TATTTCTT

CTCGCCTGTAAGTAAGTAATAAAAAAAAAAACCAATGTGCATATGAAATAGATCTTTTATACAATCTGTCCACATTAAAAAAAATAAATAAAT    700
AAATAAAT
GAGCGGACATTCATTCATTATTTTTTTTTGGTTACACGTATACTTTATCTAGAAAATATGTTAGACAGGTGTAATTTTTTTATTTATTTA
TTTATTTA

CTGAAATTTTCTTTTTATTAACAAAAATTTCAGTTTTATAACTACAGGACATTTTAGCAGTTTTTTTTCTACTGAAATTGTGCTTTTTTCAG    800
ATCTTCTT
CACTTTAAAAAAAGAAAAATAATTGTTTTTAAAGTCAAAATATTGATGTCCTGTAAAATCGTCAAAAAAAAGATGACTTTAACACGAAAAAA
GTCTAGAAGAA

TTTCCTTTTTTCTGATCTTCTGAGCTCTGTCAGGAATTACATGTGTAATTAAACTTCTTTACAGTTACACGACTGAGTTTGAAATACTTTGA    900
AATACTTT
AAAGGAAAAAAGACTAGAAGACTCGAGACAGTCCTTAATGTACACATTAATTTGAAGAAATGTCAATGTGCTGACTCAAACTTTATGAAACT
TTATGAAA
```

Fig. 3A

```
GAAATCTTCTGACATGTTTCGCTTCACTCTGAGCTCTGCTGCACATCCTGATTTCTTTTTACAAACGTTCAGTCACACATTTCATCACAAAT    1000
ATCAGCTC
CTTTAGAAGACTGTACAAAGCGAAGTGAGACTCGAGACGACGTGTAGGACTAAAGAAAAATGTTTGCAAGTCAGTGTGTAAAGTAGTGTTTA
TAGTCGAG

TTTGACGAAAAGACAGCTTGGACTTATTTTCATGTCTGTTAACGTCAGGCGTGATGGAGGATAGGAGATGCTGCATTATGTGAACACATCTT    1100
GTAAAAAA
AAACTGCTTTTCTGTCGAACCTGAATAAAAGTACAGACAATTGCAGTCCGCACTACCTCCTATCCTCTACGACGTAATACACTTGTGTAGAA
CATTTTTT

GCTGAATAAAAATGATTTCTACGACTGTTATCTGCTTTAAACTAATGAGCTGAGCAGATGGAGCAGAAGGTTAATAGCTGATCAGATCATGT    1200
CGGCTCAT
CGACTTATTTTTACTAAAGATGCTGACAATAGACGAAATTTGATTACTCGACTCGTCTACCTCGTCTTCCAATTATCGACTAGTCTAGTACA
GCCGAGTA

TAGCTTCAGTTTGTTTTACTAAGTGCTGTAACCAGTCAATCAGAAACACACTGGCACTTAATATGTGCTGATGGCAGCGCATCTGTTTGTCC    1300
ACACACAC
ATCGAAGTCAAACAAAATGATTCACGACATTGGTCAGTTAGTCTTTGTGTGACCGTGAATTATACACGACTACCGTGCCGTAGACAAACAGG
TGGGTGTG

ACACACACACACACACACACACAGATTCGTCTCGCCATCTCTTCACAGGGCTGTTCATTGACTAACGTTCAATTTCTGAAAGTTAAACCA    1400
AATCTTTC
TGTGTGTGTGTGTGTGTGTGTGTCTAAGCAGAGCGGTAGAGAAGTGTCCCGACAAGTAACTGATTGCAAGTTAAAGACTTTCAATTTGGT
TTAGAAAG

ACCTCAGGTTTAATAAATCATATTAAGGGTATTTTTGCAGAGTCCCCATAATCCGTAATCGCACACAAGTCCCCACAATGTAGGTGAAATAG    1500
GTTCCACG
TGGAGTCCAAATTATTTAGTATAATTCCCATAAAAACGTCTCAGGGGTATTAGGCATTAGCGTGTGTTCAGGGGTGTTACATCCACTTTATC
CAAGGTGC

GAAACACGTGGAACAGGGGGTGTGTCAGGTGGTGCTGGTGGAGTATAAATGGAGAGAAGGCTCTTGGTTCTGCCTCACACAGCCCAGCTGCT    1600
CCTGCCCT
CTTTGTGCACCTTGTCCCCCACACAGTCCACCACGACCACCTCATATTTACCTCTCTTCCGAGAACCAAGACGGAGTGTGTCGGGTCGACGA
GGACGGGA

TCATCTCAGAGTTACCTCCTCCTCTCTGTCTGTGCAGGTGAGTGCTGGCTGTAGGTTTGGTTGTGAGGACAGTGACTGTGATGCTAACGTGA    1700
ATGTGCTT
AGTAGAGTCTCAATGGAGGAGGAGAGACAGACACGTCCACTCACGACCGACATCCAAACCAACACTCCTGTCACTGACACTACGATTGCACT
TACACGAA

TTGTGTTCAGCTCTTTTCCAGCATG
AACACAAGTCGAGAAAAGGTCGTAC
```

Fig. 3B

```
                                             ....700bp.... GTCCCCATAATCGCACACAAGTC
CCCACAATGTAGGTGAAATAGGTTCCACGGAAACACGTGGAACAGGGGGTGTGTCCAGGTGGTGCTGGTGGAGTATAAA
TGGAGAGAAGGCTCTTGGTTCTGCCTCACACAGAAAAGCTGCTCCTGCCCTTCATCTCAGAGTTACCTCCTCCTCTCTG
TCTGTGCAGGTGAGTGCTGGCTGTAGGTTTGGTTGTGAGGACAGTGACTGTGATGCTAACGTGAATGTGCTTTTGTGTT
```

CAGCTCTTTTCCAGC ATG GCA GCG CTC TGG CTC CAG GCC TTC TCC CTG CTC GTC TTA ATG ATG
                met ala ala leu trp leu gln ala phe ser leu leu val leu met met GTT TCG TGG CCG GGC TCC CAG GCC GTC GGT GGG CCA CAG CAC CTG TGC GGC TCC CAC CTG
val ser trp pro gly ser gln ala val gly gly pro gln his leu cys gly ser his leu GTG GAT GCC CTG TAC CTG GTC TGT GGG GAC AGA GGC TTC TTC TAC AAC CCC AGG AGA GAT
val asp ala leu tyr leu val cys gly asp arg gly phe phe tyr asn pro arg arg asp GTG GAC CCT CTG CTT GGT GAGACCACCAACCACAAACAGAAACACTAGACAAACTATTTGAGGGCAGCTTTTC
val asp pro leu leu

TTTCTCTGAGTTCACTTTAAATCAGCTTTCATGTTGGAAACATGGTAATAGTAATTTTCCATATCTTTATGGACCCTAC

ATGATTAGTTTACATCTATTGCCATTTGTCTCAACACCTGCATCATATAATAGCGCTGATTTTGTAACACTTTGTGTTA

GAATTAGTAATTTATGTTCTAATAATGTTTGATATGTATTCTTTAATATAAATGACCAGAATTTTTAGATCTGAACATT

CACCTGCTCTTCATCCCATCAG   GT TTC CTC CCT CCA AAG GCA GGT GGT GCT GTG GTG CAA GGT
                            gly phe leu pro pro lys ala gly gly ala val val gln gly GGT GAG AAT GAA GTG ACC TTC AAA GAC CAG ATG GAA ATG ATG GTG AAG CGA GGC ATT GTG
gly glu asn glu val thr phe lys asp gln met glu met met val lys arg gly ile val GAG GAA TGC TGT CAC AAA CCC TGT ACC ATC TTC GAC CTG CAG AAC TAC TGC AAC TGA ACT
glu glu cys cys his lys pro cys thr ile phe asp leu gln asn tyr cys asn *

```
GCTCTGCTGGACTTTGTTTAGTCGAGCCAGGCTCGGCTATTCAGGTCTGAGTCCCAGCCCCACCTCGCTCCCTGCTTCA
GAGGAGAGCCACAGCTGTCCTCTCTCTGAAAACCAACTGCTGTCAAATGAAGTGCTGAGAAATGGATAAAATTAATTTT
CCAAGAAATAAAAATGCAAAATGTGACAACGTGAGGCAAAAAAGTGTGTTCTTTTGTTGTGATGAATTCAGTTAATTGA
TTAAAGTGAAAACTCGAACATGTTAGGTACCTGCTGCTATCCAGCACAAACTGCTGAGCTTTCACTTTCCAAAGCTTTG
TGTTTAGCTTATAGTGTCTCTGAACAGGATATAAACACATCATGCACTCTGACATGATGTCCTTTTCAAACAATCCCTT
GTCATCTTCATTTCAGCAGGTCAGTGTTTTTTATTCAGGTCCTCGTGATGACACAGAAGATAAAAACACCAAGTATTCT
AAAAATTATCAAATTGAATTTTTAAGTTCAAAAGCATTCTTCCATCACAGTCAACAGAACCCCAAGACCTGAAGTTCCAA
AGGCCTGTGGTGTTACCACTATGCTATCTACATATGTTACCTGCTTTTAACTATTAAACGGAGCAGATGGATCAGAAGG
TTAATAGCTGATCAGATCATGTCAGCTCATTAGCTTCAGTTTGTTTTACTGAGTGCTGTAACCACTCAATCAGAAACAC
ACTGTTACTTAATCTGAGTACATACTTGTATACATTAAACTTGGAAAAAGATAGATGTGAAATGTAAAAGTGAGGTCAA
TCGTCAAATGTGACACGATATTTGGATCTGTTTATCCTTCCAGGATCACGGGGCGGGGAGAGCCTATCCCAGCTACCAT
AGTGCGAGAGGTCAGGTACACCCTGGACAGGTCAACAGCCTGTCACAGGGTTTACGCTCAGAGACAAGCAACCACGCCA
CTTCGGCTTATACCAGTATTATTTCCTAAATGTTGCCAATAAAAAACAAAATCAGTAGAATTTTAAGCAGTTTTCATTT
TAATTTAACCTCATTTGAAGAAGAAGTCAGAGGTCCAAAGTATGGGAATATTTATAATTCCAATGTTGTCAATTCAAAT
AATGGCAATAAGAAACATAGTTTGAAATAGA
```

FIG. 3c

```
                                                          ....700bp.... GTCCCCATAATCGCACACAAGTC
CCCACAATGTAGGTGAAATAGGTTCCACGGAAACACGTGGAACAGGGGGTGTGTCCAGGTGGTGCTGGTGGAGTATAAA
TGGAGAGAAGGCTCTTGGTTCTGCCTCACACAGAAAAGCTGCTCCTGCCCTTCATCTCAGAGTTACCTCCTCCTCTCTG
TCTGTGCAGGTGAGTGCTGGCTGTAGGTTTGGTTGTGAGGACAGTGACTGTGATGCTAACGTGAATGTGCTTTTGTGTT
```

CAGCTCTTTTCCAGC ATG GCA GCG CTC TGG CTC CAG GCC TTC TCC CTG CTC GTC TTA ATG ATG
                met ala ala leu trp leu gln ala phe ser leu leu val leu met met GTT TCG TGG CCG GGC TCC CAG GCC TTC GTG CAG CAG CAC CTG TGC GGA TCC CAC CTG GTG
val ser trp pro gly ser gln ala PHE VAL ASN gln his leu cys gly ser his leu val GAG GCC CTG TAC CTG GTC TGT GGG GAG AGA GGC TTC TTC TAC ACC CCC AAG AGA GAT GTG
GLU ala leu tyr leu val cys gly GLU arg gly phe phe tyr THR pro LYS arg asp val GAC CCT CTG CTT G     GTGAGACCACCAACCACAAACAGAAACACTAGACAAACTATTTGAGGGCAGCTTTTC
asp pro leu leu

TTTCTCTGAGTTCACTTTAAAATCAGCTTTCATGTTGGAAACATGGTAATAGTAATTTTCCATATCTTTATGGACCCTAC

ATGATTAGTTTACATCTATTGCCATTTGTCTCAACACCTGCATCATATAATAGCGCTGATTTTGTAACACTTTGTGTTA

GAATTAGTAATTTATGTTCTAATAATGTTTGATATGTATTCTTTAATATAAATGACCAGAATTTTTAGATCTGAACATT

CACCTGCTCTTCATCCCATCAG  GT TTC CTC CCT CCA AAG GCA GGT GGT GCT GTG GTG CAA GGT
                           gly phe leu pro pro lys ala gly gly ala val val gln gly GGT GAG AAT GAA GTG ACC TTC AAA GAC CAG ATG GAA ATG ATG GTG AAG CGA GGC ATT GTG
gly glu asn glu val thr phe lys asp gln met glu met met val lys arg gly ile val GAG CAA TGC TGT ACC TCC ATT TGT TCC CTG TAC CAG CTG GAG AAC TAC TGC AAC TGA ACT
glu GLN cys cys THR SER ILE cys SER LEU TYR GLN leu GLU asn tyr cys asn *

```
GCTCTGCTGGACTTTGTTTAGTCGAGCCAGGCTCGGCTATTCAGGTCTGAGTCCCAGCCCCACCTCGCTCCCTGCTTCA
GAGGAGAGCCACAGCTGTCCTCTCTCTGAAAACCAACTGCTGTCAAATGAAGTGCTGAGAAATGGATAAAATTAATTTT
CCAAGAAATAAAAATGCAAAATGTGACAACGTGAGGCAAAAAAGTGTGTTCTTTTGTTGTGATGAATTCAGTTAATTGA
TTAAAGTGAAAACTCGAACATGTTAGGTACCTGCTGCTATCCAGCACAAACTGCTGAGCTTTCACTTTCCAAAGCTTTG
TGTTTAGCTTATAGTGTCTCTGAACAGGATATAAACACATCATGCACTCTGACATGATGTCCTTTTCAAACAATCCCTT
GTCATCTTCATTTCAGCAGGTCAGTGTTTTTTATTCAGGTCCTCGTGATGACACAGAAGATAAAAACACCAAGTATTCT
AAAAATTATCAAATTGAATTTTAAGTTCAAAAGCATTCTTCCATCACAGTCAACAGAACCCCAAGACCTGAAGTTCCAA
AGGCCTGTGGTGTTACCACTATGCTATCTACATATGTTACCTGCTTTTAACTATTAAACGGAGCAGATGGATCAGAAGG
TTAATAGCTGATCAGATCATGTCAGCTCATTAGCTTCAGTTTGTTTTACTGAGTGCTGTAACCACTCAATCAGAAACAC
ACTGTTACTTAATCTGAGTACATACTTGTATACATTAAACTTGGAAAAAGATAGATGTGAAATGTAAAAGTGAGGTCAA
TCGTCAAATGTGACACGATATTTGGATCTGTTTATCCTTCCAGGATCACGGGGCGGGGAGAGCCTATCCCAGCTACCAT
AGTGCGAGAGGTCAGGTACACCCTGGACAGGTCAACAGCCTGTCACAGGGTTTACGCTCAGAGACAAGCAACCACGCCA
CTTCGGCTTATACCAGTATTATTTCCTAAATGTTGCCAATAAAAAACAAAATCAGTAGAATTTTAAGCAGTTTTCATTT
TAATTTAACCTCATTTGAAGAAGAAGTCAGAGGTCCAAAGTATGGGAATATTTATAATTCCAATGTTGTCAATTCAAAT
AATGGCAATAAGAAACATAGTTTGAAATAGA
```

FIG. 4

```
                                                       ....700bp.... GTCCCCATAATCGCACACAAGTC
CCCACAATGTAGGTGAAATAGGTTCCACGGAAACACGTGGAACAGGGGGTGTGTCCAGGTGGTGCTGGTGGAGTATAAA
TGGAGAGAAGGCTCTTGGTTCTGCCTCACACAGAAAAGCTGCTCCTGCCCTTCATCTCAGAGTTACCTCCTCCTCTCTG
TCTGTGCAGGTGAGTGCTGGCTGTAGGTTTGGTTGTGAGGACAGTGACTGTGATGCTAACGTGAATGTGCTTTTTGTGTT
```

CAGCTCTTTTCCAGC ATG GCA GCG CTC TGG CTC CAG GCC TTC TCC CTG CTC GTC TTA ATG ATG
                met ala ala leu trp leu gln ala phe ser leu leu val leu met met GTT TCG TGG CCG GGC TCC CAG GCC TTC GTG CAG CAG CAC CTG TGC GGA TCC CAC CTG GTG
val ser trp pro gly ser gln ala PHE VAL ASN gln his leu cys gly ser his leu val GAG GCC CTG TAC CTG GTC TGT GGG GAG AGA GGC TTC TTC TAC ACC CCC AAG ACC AGA GAT
GLU ala leu tyr leu val cys gly GLU arg gly phe phe tyr THR pro LYS THR arg asp GTG GAC CCT CTG CTT G GTGAGACCACCAACCACAAACAGAAACACTAGACAAACTATTTGAGGGCAGCTTTTC
val asp pro leu leu

TTTCTCTGAGTTCACTTTAAATCAGCTTTCATGTTGGAAACATGGTAATAGTAATTTTTCCATATCTTTATGGACCCTAC

ATGATTAGTTTACATCTATTGCCATTTGTCTCAACACCTGCATCATATAATAGCGCTGATTTTGTAACACTTTGTGTTA

GAATTAGTAATTTATGTTCTAATAATGTTTGATATGTATTCTTTAATATAAATGACCAGAATTTTTAGATCTGAACATT

CACCTGCTCTTCATCCCATCAG   GT TTC CTC CCT CCA AAG GCA GGT GGT GCT GTG GTG CAA GGT
                         gly phe leu pro pro lys ala gly gly ala val val gln gly GGT GAG AAT GAA GTG ACC TTC AAA GAC CAG ATG GAA ATG ATG GTG AAG CGA GGC ATT GTG
gly glu asn glu val thr phe lys asp gln met glu met met val lys arg gly ile val GAG CAA TGC TGT ACC TCC ATT TGT TCC CTG TAC CAG CTG GAG AAC TAC TGC AAC TGA ACT
glu GLN cys cys THR SER ILE cys SER LEU TYR GLN leu GLU asn tyr cys asn  *

```
GCTCTGCTGGACTTTGTTTAGTCGAGCCAGGCTCGGCTATTCAGGTCTGAGTCCCAGCCCCACCTCGCTCCCTGCTTCA
GAGGAGAGCCACAGCTGTCCTCTCTCTGAAAACCAACTGCTGTCAAATGAAGTGCTGAGAAATGGATAAAATTAATTTT
CCAAGAAATAAAAATGCAAAATGTGACAACGTGAGGCAAAAAAGTGTGTTCTTTTGTTGTGATGAATTCAGTTAATTGA
TTAAAGTGAAAACTCGAACATGTTAGGTACCTGCTGCTATCCAGCACAAACTGCTGAGCTTTCACTTTCCAAAGCTTTG
TGTTTAGCTTATAGTGTCTCTGAACAGGATATAAACACATCATGCACTCTGACATGATGTCCTTTTCAAACAATCCCTT
GTCATCTTCATTTCAGCAGGTCAGTGTTTTTTATTCAGGTCCTCGTGATGACACAGAAGATAAAAACACCAAGTATTCT
AAAAATTATCAAATTGAATTTTAAGTTCAAAAGCATTCTTCCATCACAGTCAACAGAACCCCAAGACCTGAAGTTCCAA
AGGCCTGTGGTGTTACCACTATGCTATCTACATATGTTACCTGCTTTTAACTATTAAACGGAGCAGATGGATCAGAAGG
TTAATAGCTGATCAGATCATGTCAGCTCATTAGCTTCAGTTTGTTTTACTGAGTGCTGTAACCACTCAATCAGAAACAC
ACTGTTACTTAATCTGAGTACATACTTGTATACATTAAACTTGGAAAAAGATAGATGTGAAATGTAAAAGTGAGGTCAA
TCGTCAAATGTGACACGATATTTGGATCTGTTTATCCTTCCAGGATCACGGGGCGGGGAGAGCCTATCCCAGCTACCAT
AGTGCGAGAGGTCAGGTACACCCTGGACAGGTCAACAGCCTGTCACAGGGTTTACGCTCAGAGACAAGCAACCACGCCA
CTTCGGCTTATACCAGTATTATTTCCTAAATGTTGCCAATAAAAAAACAAAATCAGTAGAATTTTAAGCAGTTTTCATTT
TAATTTAACCTCATTTGAAGAAGAAGTCAGAGGTCCAAAGTATGGGAATATTTATAATTCCAATGTTGTCAATTCAAAT
AATGGCAATAAGAAACATAGTTTGAAATAGA
```

FIG. 5

TRANSGENIC TILAPIA COMPRISING A HUMANIZED INSULIN GENE

RELATED APPLICATIONS

This application is a continuation-in-part of U.S. application Ser. No. 08/750,391, filed on Mar. 22, 1996, now U.S. Pat. No. 6,015,713 which is a 35 USC 371 National Stage filing of PCT/CA96/00171 filed on Mar. 22, 1996 and a continuation of U.S. application Ser. No. 08/416,866, filed on Apr. 19, 1995, now U.S. Pat. No. 5,588,708.

TECHNICAL FIELD

This invention relates to transgenic fish containing a modified fish insulin gene which has been altered to produce humanized insulin. This invention further relates to improved methods for the xenotransplantation of transgenic islets in the treatment of diabetes. In a further aspect, the present invention relates to improved methods for mass isolation of fish islets.

BACKGROUND OF THE INVENTION

Diabetes mellitus is a disease resulting in significant morbidity and mortality. The total annual direct and indirect costs of diabetes in the Unites States exceeds $90 billion dollars. Insulin-dependent diabetes mellitus (IDDM), because it occurs in a younger population than non-IDDM, accounts for a disproportionate percentage of these costs. Although the acute manifestations of IDDM can be controlled with daily insulin injections, most patients eventually develop sequelae such as blindness, nephropathy, neuropathy, microangiopathy, and cardiovascular disease. Substantial evidence suggests that meticulous control of glycemia will prevent or minimize these sequelae.

A more physiological method of treating diabetes would be pancreas or islet transplantation. Whole or segmental pancreas transplantation has been performed successfully in man and some preliminary evidence suggests that this technique will prevent the sequelae of diabetes in man. However, pancreas transplantation is not trivial surgery; it poses problems with drainage of exocrine secretions and requires a lifetime of immunosuppressive therapy. On the other hand, islet transplantation has certain theoretical advantages, particularly related to the ease of surgery, the absence of extraneous exocrine tissue, and the cryopreservability of isolated islets. More importantly, islets are more amenable to immunoalteration. Indeed, various methods have been developed to prolong allograft survival without continuous immunosuppression in rats and mice. The ability to transplant islets without continuous immunosuppression may eventually prove absolutely necessary in man because many immunosuppressive drugs are somewhat toxic to islets.

Recent improvements in the methods of mass islet isolation and several recent clinical reports suggest that islet transplantation is on the verge of becoming a feasible treatment for IDDM. However, several obstacles exist. First, islets comprise only 2% of the human pancreas; yields from human "islet isolation" procedures are extremely variable and several human donor pancreases are often required to generate sufficient islets for a single transplant. Thus, there are insufficient human donor pancreases available to treat the vast numbers of type I diabetic patients. Second, islet allograft rejection has proven difficult to manage using conventional methods and, unfortunately, the majority of islet allografts are quickly lost. Therefore, it seems likely that widespread implementation of islet transplantation would require the development of islet xenotransplantation methods.

In response to this eventuality, many biomedical corporations are spending millions of dollars developing and patenting "bio-artificial pancreas" technologies (i.e., microencapsulation or macroencapsulation of islet tissue). The underlying concept behind these approaches is that the islet tissue is protected from the immune system by a membrane with pore sizes small enough to prevent immunocytes and antibodies from damaging the graft yet large enough for insulin, oxygen, glucose, and nutrients to pass freely.

During the past few years, several clinical islet transplantation centers have devoted extensive effort to the development of experimental islet xenotransplantation models using large animals as donors. Most of these studies have centered on porcine, bovine, canine, or non-human primate islets. However, the pancreata in these species, like the human pancreas, are fibrous and do not readily yield large quantities of intact, viable islet tissue. Moreover, generation of islet preparations from large animal donors is expensive and islet yields are variable.

Brockmann bodies are anatomically discrete organs in certain teleost fish. Teleost fish insulin has been used in certain cases to maintain human diabetics (Wright, J R Jr., Experimental transplantation using principal islets of teleost fish Brockmann Bodies. *Pancreatic Islet Cell Transplantation: 1892–1992—One Century of Transplantation for Diabetes,* edited by C. Ricordi, R. G. Landes Co., Austin, 1992, p. 336–351). However, it is likely that the immunogenicity of teleost insulin may prevent clinical application for BB xenotransplantation. On the other hand, the production of transgenic fish whose BBs produce humanized insulin may circumvent this problem. Transgenic fish having BBs that physiologically secrete humanized insulin would eliminate the need for human pancreatic donors and procedures for the isolation of islets therefrom.

Until recently, BBs were harvested manually by microdissection while being visualized through a dissecting microscope inside a laminar flow hood (Wright J R Jr. Preparation of Fish Islets (Brockmann bodies) In: Lanza R P; W L Chick, eds. *Pancreatic Islet Transplantation genes* Vol. 1. *Procurement of Pancreatic Islets.* Austin: RG Landes co.; (1994:123–32)). While this is much easier and less expensive than the standard procedure of harvesting islets from rodents, it is a time consuming and tedious task. Although it is easy to harvest sufficient islets to perform xenografts in mice, this method is not well suited to harvest large volumes of islet tissue as would be required for clinical use or large animal studies. Furthermore, microdissection allows collection of less than 50% of the islet tissue per donor fish (i.e., those large BBs that are easily visible with the naked eye). Therefore, development of a more efficient method of harvesting BBs would be critical for the future application of fish islets as a donor source for clinical and experimental use.

To date, transgenic fish technology has been used to produce hardier fish that will grow rapidly and will tolerate adverse environments (Hackett P B: The molecular biology of transgenic fish. In: *Biochemistry and molecular Biology of Fishes* 2, Hochachka P and Mommesen T (eds.) Amsterdam: Elsevier, 1993; and Hackett P B: The molecular biology of transgenic fish. In: *Biochemistry and molecular Biology of Fishes* 2, Hochachka P and Mommesen T (eds.) Amsterdam: Elsevier, 1993). Most of these efforts have been directed at insertion of growth hormone transgenes. Another approach has been to insert antifreeze genes from species that tolerate very cold waters (i.e., such as winter flounder) into other species so that they will not only survive, but actually thrive in colder water. This approach permits aquaculture in more northerly regions and allows aquaculture stocks to grow year-round, rather than just during the summer growth season.

Accordingly, there exists a need for a method to supplement human islets with islets from other species without provoking an immune response. In addition, there exists a need in the art for improved methods of harvesting islets for use in xenotransplantation.

OBJECTS OF THE INVENTION

The objectives of the present invention are to provide a genetically stable production strain of transgenic tilapia for use in tissue transplantation. This line should have the following properties: (1) stable integration of humanized insulin gene in Teleost fish, (2) production of insulin in transgenic Teleosts under physiological glucose regulation, (3) absence of humanized tilapia DNA sequences other than the insulin locus, (4) homozygosity for the humanized insulin gene at the tilapia insulin locus, (5) genetic and developmental stability and uniformity, (6) good growth and survival characteristics, and (7) genetic identifiability for security against contamination and for protection of the proprietary interests of the developers.

These and other objects of the invention will become apparent upon review of the following description of the invention and appended claims.

SUMMARY OF THE INVENTION

This invention relates to a humanized tropical fish insulin gene capable of being physiologically expressed in a tropical fish islet cell. By virtue of the similarity between fish and human insulin, it has been possible to modify a fish insulin gene to encode a protein having the same alpha and beta chains as a human insulin while using fish-preferred codons. The humanized fish gene thus comprises a coding sequence of a humanized insulin gene under the control of regulatory sequences of the tropical fish insulin gene. In this manner, the protein processing machinery of the fish islet cell operates to process the initial translation product to yield a fully-formed humanized insulin polypeptide that is biologically active and substantially non-immunogenic in humans.

In another aspect, the present invention also relates to the preparation of transgenic tropical fish whose islet cells secrete humanized insulin. In a preferred embodiment, the tropical fish is a teleost fish such as tilapia.

In another embodiment, the present invention is directed to a unique animal model for islet xenotransplantation utilizing tilapia, a teleost fish, as islet donors (Wright, J R Jr., supra). The islet tissue in certain teleost fish, called principal islets or Brockmann bodies (BBs), is anatomically distinct from their pancreatic exocrine tissue and can be easily identified macroscopically. Thus, the islets can be readily isolated using straightforward techniques rather than expensive islet isolation procedures, such as is required when procuring islet tissue from mammalian pancreases. Tilapia islets transplanted into diabetic nude mice have been observed to produce long-term normoglycemia and a mammalian-like glucose tolerance curve (Wright, J R Jr., Polvi S. and Maclean H: Experimental transplantation using principal islets of teleost fish (Brockmann bodies): Long-term function of tilapia islet tissue in diabetic nude mice. Diabetes 41:1528–32.1992).

BRIEF DESCRIPTION OF THE DRAWINGS

FIG. 1 presents an amino acid sequence of tilapia insulin hormone determined by automated Edman degradation. The amino acid sequence of the tilapia A chain and B chain is illustrated in SEQ ID NO:1 and 2, respectively.

FIG. 2 presents a comparison of the primary structure of tilapia insulin with human insulin. (–) represents sequence identity. The amino acid sequence of the A chain and B chain human insulin sequence is illustrated in SEQ ID NO: 3 and 4, respectively.

FIGS. 3A and 3B show the approximately 1.8 kb of DNA upstream of the start codon for the amino acid sequence of tilapia insulin gene, and ending with the start codon for the amino acid sequence of tilapia insulin gene. This DNA sequence and that of FIG. 3C are also shown in SEQ ID NO: 5.

FIG. 3C shows a DNA and corresponding amino acid sequence of tilapia insulin gene, including some of the untranslated upstream DNA and approximately 1 kb of sequence downstream from the coding sequence. The DNA and amino acid sequence is also shown in SEQ ID NOS: 5 and 14.

FIG. 4 shows a DNA and corresponding amino acid sequence of a first humanized tilapia insulin gene. The DNA and amino acid sequence is also shown in SEQ ID NOS: 6 and 15.

FIG. 5 shows a DNA and corresponding amino acid sequence of a second humanized tilapia insulin gene. The DNA and amino acid sequence is also shown in SEQ ID NOS: 7 and 16.

DETAILED DESCRIPTION OF THE INVENTION

In accordance with the present invention, there are provided isolated polynucleotides encoding a humanized tropical fish insulin gene, polypeptides encoded by said polynucleotides and antibodies to said polypeptides, and fragments thereof, wherein said humanized insulin gene encodes an insulin protein that is biologically active and substantially non-immunogenic in humans.

In another embodiment of the present invention there are provided humanized insulin gene(s) that is/are expressed in tropical fish islet cells, wherein said gene comprises a coding sequence of an insulin gene under the control of regulatory sequences of the tropical fish insulin gene, wherein said humanized insulin gene encodes a humanized teleost insulin protein that is biologically active and substantially non-immunogenic in humans.

Any fish insulin gene is suitable for use in the practice of the present invention, however, it is presently preferred that the tropical fish insulin gene is isolated from a fish having one or more discrete principal islets composed of relatively pure endocrine tissue and which are able to tolerate culture at 37° C. Yang, et al., Immunocytochemical Characterization of the Pancreatic Islet Cells of the Nile Tilapia, Gen. and Comp. Endocrinol. 114:47–56 (1999). As used herein, "relatively pure" means that a majority of the surrounding exocrine tissue has been digested away or otherwise removed. In one embodiment, the resulting islets are greater than about 90% pure (i.e., less than 10% exocrine tissue). In another embodiment, the resulting islets are greater than about 95% pure. In a presently preferred embodiment, the resulting silets are greater than about 99% pure. Suitable fish include teleost fish such as tilapia, *Osphoronemus gourami, Colossoma macroponum, Piaractus mesopotamicus,* and the like.

The term "humanized insulin gene," as used herein means a modified fish insulin gene (e.g., from tilapia, or the like) that contains a sufficient portion of the human insulin coding sequence to produce a humanized insulin product. A humanized insulin product will thus be biologically active when transplanted into a human and will also contain sufficient human insulin sequences to minimize or avoid destruction of the humanized insulin product by the human immune system. In a preferred embodiment the humanized insulin gene encodes the alpha chain and at least the first 29 amino acids of the beta chain of human insulin.

Humanized (or modified) insulin genes contemplated for use herein further contain a sufficient portion of the regulatory sequences of the tropical fish insulin gene for expression of the humanized gene in tropical fish islet beta cells. In a presently preferred embodiment, the regulatory regions include all enhancers naturally present in the tilapia insulin gene. In another embodiment, the tilapia regulatory regions are not modified, so as to allow normal regulatable expression of the humanized gene. Of course, those of skill in the art recognize that modifications to the tilapia regulatory regions may include incorporation of additional sequences that enhance expression over normal levels.

In one embodiment of the present invention the humanized insulin gene comprises a tilapia insulin gene wherein 9 codons in the A chain are changed, as are 8 codons in the B chain. As further described below, the substituted codons are devised so that they code for the human insulin chains using tilapia preferred codons. Neither the tilapia pre-insulin leader nor the C chain is altered.

Because only a limited number of codons of the fish insulin genes need to be changed to encode humanized insulin, additional embodiments of the present invention comprise humanized fish insulin genes having varying levels of identity with the human insulin gene. Thus, in another embodiment of the present invention there is provided a humanized insulin gene wherein the coding sequence of the insulin gene encodes the alpha chain and at least the first 29 amino acids of the beta chain of human insulin.

In one embodiment the coding sequence of the humanized insulin gene encodes the alpha chain and the beta chain of human insulin. In another embodiment the humanized insulin gene comprises the DNA sequence shown in SEQ ID NO:6. In yet another embodiment, the humanized insulin gene comprises the DNA sequence shown in SEQ ID NO:7. Modifications intended to be within the scope of the invention include modifications or substitutions to the sequence of the humanized insulin gene which do not substantially affect the biological activity or enhance the immunogenicity of the insulin product in humans.

The term "polynucleotide" or "nucleic acid sequence" refers to a polymeric form of nucleotides at least 10 bases in length. By "isolated polynucleotide" or "substantially pure nucleotide" is meant a polynucleotide that is not immediately contiguous with either of the nucleic acid sequences with which it is immediately contiguous (one on the 5' end and one on the 3' end) in the naturally occurring genome of the organism from which it is derived, and includes polynucleotides substantially free of other nucleic acids, proteins, lipids, carbohydrates or other materials with which it is naturally associated. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

The polynucleotides of the invention can be ribonucleotides, deoxyribonucleotides, or modified forms of either nucleotide. The term includes single and double-stranded forms of DNA. Polynucleotide sequences of the invention include DNA, cDNA and RNA sequences which encode humanized insulin genes described herein. It is understood that the present invention embraces polynucleotides encoding all or varying portions of humanized insulin genes described herein, as long as they encode a polypeptide with insulin activity. Such polynucleotides include naturally occurring, synthetic, and modified polynucleotides as well as splice variants. For example, portions of the mRNA sequence may be altered due to alternate RNA splicing or the use of alternate promoters for RNA transcription. Alterations in humanized insulin nucleic acid include intragenic mutations (e.g., point mutation, nonsense (stop), antisense, splice site and frameshift), heterozygous or homozygous deletions, and the like. Detection of such alterations can be done by standard methods known to those of skill in the art including sequence analysis, Southern blot analysis, PCR based analyses (e.g., multiplex PCR, sequence tagged sites (STSs)), in situ hybridization, and the like.

In another embodiment of the present invention there are provided substantially pure polypeptide(s) encoded by any of the humanized genes described herein. In one embodiment, invention polypeptides comprise the amino acid sequence of SEQ ID NO:8, or antigenic fragments thereof, as well as conservatively substituted variations thereof. In another embodiment, invention polypeptides comprise the amino acid sequence of SEQ ID NO:9, or antigenic fragments thereof, as well as conservatively substituted variations thereof. Modifications intended to be within the scope of the invention include modifications or substitutions to the sequence of the humanized insulin gene which do not substantially affect the biological activity or enhance the immunogenicity of the insulin product in humans.

As used herein, "antigenic fragments" means a polypeptide of sufficient size to provoke an immune response in a host organism (i.e., an organism such as mice, rabbits, horses, or the like, that is commonly used to generate antibodies for research and therapeutic purposes). It is well accepted among those of skill in the art that a polypeptide fragment as small as in the range of about 10 up to about 15 amino acids can elicit an immune response, thereby rendering such polypeptides useful for generating antibodies thereto. See, e.g., Harlowe, E. and Lane, D., Antibodies, A Laboratory Manual, (Cold Spring Harbor Laboratory, 1988, incorporated herein by reference).

The term "substantially pure" as used herein refers to polypeptide which is substantially free of other proteins, lipids, carbohydrates or other materials with which it is naturally associated. One skilled in the art can purify invention polypepeptides using standard techniques for protein purification. Typically, the polypeptide is substantially pure when it is at least 60% by weight invention polypeptide, as opposed to other proteins and naturally-occurring organic molecules with which it is naturally associated. Preferably, the preparation is at least 75%, more preferably at least 90%, and most preferably at least 99%, by weight, invention polypeptide. A substantially pure invention polypeptide may be obtained, for example, by extraction from a source organism (e.g., a fish); by expression of a recombinant nucleic acid encoding the polypeptide; by chemically synthesizing the protein, or the like. Purity can be measured by any appropriate method, e.g., column chromatography, polyacrylamide gel electrophoresis, by HPLC analysis, or the like. The purity of the polypeptide can be verified by amino acid sequence analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

In another embodiment of the present invention there are provided isolated tilapia beta islet cells from Brockmann bodies. Such cells contain a humanized insulin gene as described herein and secrete insulin in a glucose dependent fashion. Thus, in yet another aspect, the islet cells can be administered to a subject (i.e., a heterologous host organism (e.g., humans)) to help maintain normoglycemia in the subject.

In another embodiment of the present invention the islet cells described herein are encapsulated. Encapsulation can provide for reduced or eliminated immunogenicity when introduced into a heterologous host organism. Techniques for encapsulating cells are well known to those of skill in the art.

In order to have a source of fish islets that produce and secrete humanized insulin, it is desirable to generate transgenic fish that have introduced into their genome a gene encoding humanized insulin as described herein. The term "transgenic" is used to describe an animal which includes exogenous genetic material. A "transgenic" animal can be produced by inserting the gene into the nucleus of newly fertile ova, selecting for incorporation, and then breeding positives.

Thus, in another embodiment of the present invention, there are provided transgenic fish containing the polynucleotide(s) described herein. In another embodiment of the present invention there are provided fish expressing polypeptides as described herein. In one aspect of this embodiment, the polypeptide is active in fish and thus is useful to promote growth in fish.

Various methods can be employed to make the transgenic animals of the present invention. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection, microinjection, or the like, followed by reintroduction of the stem cells into the embryo where they colonize and contribute to the germ line. Methods for microinjection of mammalian species are described in U.S. Pat. No. 4,873,191, incorporated by reference herein in its entirety and applied to fish. In yet another such method, embryonic cells are infected with a retrovirus containing the transgene whereby the germ cells of the embryo have the transgene chromosomally integrated therein.

Transgenes can be introduced into embryonal target cells at various developmental stages. Different methods are used depending on the stage of development of the embryonal target cell. The zygote is a presently preferred target for microinjection. The use of zygotes as a target for gene transfer has a major advantage in that in most cases the injected DNA will be incorporated into the host gene before the first cleavage (Brinster et al, *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

In yet another embodiment of the present invention, there are provided methods for islet xenotransplantation utilizing fish as islet donors. Fish contemplated for use as donors include teleost fish such as tilapia, *Osphoronemus gourami, Colossoma macroponum, Piaractus mesopotamicus,* and the like. Recipient animals include mammals such as mice, rats, humans, and the like. Transplantation methods are further described in the examples below.

Islet cells contemplated for transplantation include those that contain and are capable of expressing humanized insulin genes as described herein. Accordingly, in another embodiment of the present invention, there are provided methods for treating diabetes in a subject, said method comprising transplanting into said subject islet cells containing humanized insulin genes as described herein, and are capable of expressing same. Insulin produced by the transplanted islets will be secreted by the islet cells.

Hemoglobin A1c (HbA1c) is a minor component of the normal human constituency of hemoglobin variants. HbA1c is formed by the non-enzymatic attachment of glycosyl to the amino-terminus of HbA3. Although HbA1c accumulates normally during the lifespan of circulating red blood cells, HbA1c concentrations are approximately twice normal levels in people with diabetes. Monitoring of HbA1c concentration is an indirect, yet accurate, way of measuring blood glucose levels and is thereby useful in monitoring those with diabetes and pre-diabetic conditions. Therefor, a composition useful for increasing insulin sensitivity and/or otherwise lowering blood glucose levels will concomitantly reduce HbA1c concentrations.

Thus, in accordance with another aspect of the present invention, there are provided methods for reducing HbA1c concentrations in those with diabetes mellitus and its precursor conditions, such as impaired glucose tolerance (IGT) and the like, said method comprising transplanting into said subject islet cells containing and expressing humanized insulin genes as described herein, and are capable of expressing same.

In accordance with yet another aspect of the present invention, there are provided improvements over methods involving administration of insulin for the treatment of a subject having diabetes, or its precursor conditions, such as IGT, and the like, the improvement comprising transplanting into said subject an HbA1c reducing amount of islet cells containing humanized insulin genes as described herein, and which are capable of expressing same.

The invention will now be described in greater detail in the following non-limiting examples.

EXAMPLE 1

Selection of Appropriate Donor Species

When selecting a fish donor species for xenotransplantation one should consider the following seven criteria. First, the fish should be easily bred. Second, it should be large enough to work with easily. Third, the fish species should have one or more discrete Brockmman Bodies (BBs) composed of relatively pure endocrine tissue. Fourth, the BBs must be able to tolerate culture at 37° C., the body temperature of the host, without undergoing necrosis, degranulation, or loss of function. Fifth, the species should maintain fasting plasma glucose levels in a mammalian range. Sixth, insulin secretion must be glucose dependent. And finally, the BBs must be able to maintain long-term normoglycemia after transplantation into diabetic nude mice.

In a preferred embodiment of the present invention, a warm water teleost fish is used as donor species. Phylogenetically, teleosts are a large and diverse infraclass of bony fish containing more than 30,000 species. Brockmann bodies tend to occur only in "higher" teleosts; other teleosts tend to have disseminated islets. Tilapia (*Oreochromis nilotica*) and the giant gorami (*Osphronemus gorami*) are examples of tropical higher teleosts. Other tropical fish species having anatomically distinct islet tissue such as tambaqui (*Colossoma macropomum*) and Pacu (*Piractus mesopotamicus*) may also be used as donor species.

The primary structure of teleost insulins varies from that of man. Several teleost insulins have been purified and their amino acid sequences determined. All have an extra residue at the beginning of the B chain and are missing residue 30 at the end of the B chain; substitutions may occur at various other residues on both the A chain (e.g., 9 aa substitutions between human and cod insulin) and B chain (6 aa—human and cod). Most teleost fish insulins exhibit one-third to one-half the biological potency of human insulin (Nguyen T M, Wright J R Jr, Nielson P F, and Conlon J M: Characterization of the pancreatic hormones from the Brockmann body of the tilapia-implications for islet xenograft studies. Comp. Biochem. and Physiol. 111C:33–44, 1995).

EXAMPLE 2

Preparation of Humanized Insulin Gene

Tilapia insulin has been purified and sequenced (Nguyen T M, Wright J R Jr, Nielson P F, and Conlon J M: Characterization of the pancreatic hormones from the Brockmann body of the tilapia-implications for islet xenograft studies. Comp. Biochem. and Physiol. 111C:33–44, 1995) (FIG. 1). Tilapia insulin differs from human insulin by nine amino acids in the A-chain and eight amino-acids in the B-chain (FIG. 2).

Using an in vitro polymerase chain reaction (PCR) cloning strategy (Takara Shuzo Co. LTD) and nested degenerate primers based on conserved amino acids from human and several teleost fish insulins (Hobart P M, Shen L-P, Crawford R. Pictet R L and Ruttner W J: Comparision of the nucleic acid sequence of anglerfish and mammalian insulin mRNA's from cloned CDNA's. Science 210:1360–3, 1980; Chan S J, Cao Q-P, Nagamatsu S, and Steiner D F: Insulin and insulin-like growth factor genes in fishes and other primitive chordates. In: *Biochemistry and molecular Biology of Fishes*, 2, Hochachka P. and Mommesen T. (eds.) Amsterdam: Elsevier, 1993, pp. 407–17; Steiner D F: Structure and evolution of the insulin gene. Ann. Rev. Genet. 19: 463–84, 1985), the entire tilapia insulin gene has been cloned, including both 1.8 kb of 5' untranslated and 1.2 kb of 3' untranslated sequence (FIGS. 3A and 3B and SEQ ID NO:5). The complete coding regions, including the leader sequence, B chain, C-peptide, and A chain have been sequenced. In comparison to human insulin, the tilapia A chain has 13/21 identical amino acids (61.9%) and 5 of the substituted amino acids are conserved changes. The B chain has 22/29 identical amino acids (75.8%) and 3 conserved changes when compared to the human protein. (Mansour, et al., Cloning, sequencing and characterization of the tilapia insulin gene, Comp. Bioch. and Phys., Part B 121:291–297 (1998), incorporated by reference herein in its entirety). As expected, the tilapia C chain has little identity with the human C chain. The genomic structure of all known insulin genes contains an intron in the C chain. As expected, the tilapia insulin gene contains a 316 bp intron after the seventh amino acid in the C chain (phase 1). This intron has the proper GT/AG splicing donor/acceptor sequences. The 1.8 kb 5' upstream sequence of the tilapia clone obtained herein should contain all the regulatory units so the gene is regulated (i.e. glucose responsive) in a tissue specific manner similar to its native counterpart.

To determine the potential transcriptional start site, a reverse primer (IN-6, SEQ ID NO: 11) was used in a primer extension analysis. Two potential (one prominent) transcription start sites were located 72 and 76 bases (position –145 and 149 on genomic DNA) from the translational start site. A potential TATA box was found 30 bases from the upstream transcriptional start site. In general most genes that contain TATA boxes in their promoters usually initiate transcription within 25 bp. The transcriptional start sites of both trout (Argenton, F., et al., FEBS Letters, 407:191 (1997)) and salmon (Koval, A. P., et al., Nucl. Acids Res., 17:1758 (1989)) align perfectly with the second, more prominent, transcriptional start site of tilapia.

The elements responsible for insulin gene expression are primarily located within the region including the promoter (i.e. 100 bp upstream from the transcriptional initiation site) upstream to the 5' enhancers (within 300 bp upstream from the transcriptional initiation site) (Clark, A. R. and Docherty, K., J. Endorcrinol., 136:187 (1993); Stein, R., TEM, 4:96 (1993)). Many of the upstream control regions have been mapped and characterized from various species. Many of them have also been shown to be important in regulating insulin expression in vivo (Dandoy-Dron, F., et al., Differentiation, 58:291–295 (1995)). Nearly all insulin genes sequenced to date contain an insulin control element (ICE) which has the sequence GCCATCTG and is found at position –241 to –233 in the rat insulin gene. The tilapia gene contains the ICE element GCCATCT<u>C</u> with a one base substitution (underlined) at nearly the identical position (–238 to –230) (Mansour, et al., supra). The ICEs are presently grouped under the E box control elements containing the sequence CANNTG (Ephrussi, A., et al., Science, 227:134 (1985)). Two more potential E box sequences are found in the tilapia gene: positions –69 to –64 (CACGTG) and position –294 to–289 (CATCTG). The E box at position –69 is also flanked by two short (GGAA) direct repeats. A potential AP1 site (GGTGTCAG) with a one base pair missmatch (TGTGTCAG) is located at position –53 in the tilapia promoter. The tilapia insulin gene also contains several potential A elements and one C element (Mansour, et al., supra). Interestingly, the 5' upstream region (–282 to –249) contains a microsatellite comprised of 17 "CA" repeats.

Using site-directed mutagenesis and linker substitutions, the tilapia insulin gene was humanized so that it contains exons which code for human insulin while still maintaining all of the tilapia regulatory (non-coding) sequences. The substituted codons were devised so that they encode human insulin chains but still use tilapia preferred codons in order to achieve proper protein expression. The first of the humanized tilapia genes lacks the human terminal threonine on the B chain (i.e., like tilapia) (FIG. 4 and SEQ ID NO:6); this will guarantee proper cleavage of the B-C chain. The second construct contains the terminal B chain threonine (SEQ ID NO:7). The tilapia pre-insulin leader and the C chain were not altered. This construct maintains all the similar recognition sites for the endopeptidases and, therefore, transgenic fish process this modified protein as the native insulin.

EXAMPLE 3

Testing Expression of the Humanized Tilapia Insulin Gene

As described above, using site-directed mutagenesis and linker substitutions the tilapia insulin gene was "humanized". In so doing, 9 codons in the A chain were changed, as where 8 codons in the B chain. The substituted codons were devised so that they code for the human insulin chains using tilapia preferred codons. Neither the tilapia pre-insulin leader nor the C chain was altered. This construct therefor maintains all the similar recognition sites for the endopeptidases and, thus, transgenic fish should process this modified protein in the same way as they process native insulin.

Two versions of the humanized tilapia gene have been constructed. The first construct lacks the human terminal threonine on the B chain (like tilapia). This should facilitate proper cleavage of the B-C chain. The second construct contains the terminal B chain threonine. In other fish (Salmon, Carp and Anglerfish) the B chain carboxy terminal amino acid is lysine (e.g., . . . YNPK-RDVD . . . (SEQ ID NO:8)) (Hobart, P. M., et al., Science, 210:1360 (1980)) where cleavage is thought to occur by a trypsin-like activity (at the dash line in the example). In tilapia this lysine is substituted by an arginine (e.g., YNPR-RDVD . . . (SEQ ID NO:9)). Since arginine and lysine are similar amino acids in structure and charge (i.e., a conserved substitution), it is likely that a similar enzyme is involved in cleavage of the B-C chain. In humans, however, the B chain COOH terminal amino acid is threonine (YTPKT-RR-EAEDL . . . (SEQ ID NO:10)) (id.) where cleavage is thought to occur by a trypsin-like activity (dash lines in the example). Cleavage occurs by way of a PC 3 endopeptidase after the two arginines (second dash on the example) followed by a carboxypeptidase that removes both of these arginines (Halban, P A, Trends Endocrinol. Metabol. 1:260, 1990). Thus, by an analogous method, cleavage may initially occur after the two arginines (e.g., YNPRR-DVD . . . (SEQ ID NO:9)) in tilapia, and after the lysine arginine (YNPKR-DVD . . . (SEQ ID NO:8)) in all other fish, followed by a carboxypeptidase which only removes one arginine due to the penultimate proline which may interfere with further cleavage (Halban, P. A. Trends in Endocrinol. Metabolism, 1:261 (1990)). If cleavage occurs according to this latter mechanism, a terminal threonine (as found in humans or in one of the constructs described herein) would still be properly processed.

The two humanized versions and also the native tilapia insulin gene have been produced in *E.coli*. All three genes were expressed in the prokaryotic expression vector pRSET (Invitrogen, Carlsbad, Calif.). These proteins are fused to a 6 histidine tag to allow rapid purification (using Ni-agarose) and detection. By exposure to sonicated BBs, the enzymes contained therein operate to correctly process the insulin, the "mature" insulin molecules will be reattached to the Ni-agarose, purified by separation from the cellular proteins and then detected by suitable means, e.g., Western blotting, HPLC, or the like. Correct processing is confirmed by a change in size of the protein, as detected by Western blot.

Presently, it is preferred to produce a humanized tilapia insulin that is identical to human insulin using the +Threonine construct. Alternatively, transgenic fish can be created using the humanized –Threonine insulin gene produced by microinjection, as described herein. Based upon the known activity of porcine insulin in man (i.e., which differs from human insulin only at the carboxy terminus of the B-chain), either form of humanized insulin is expected to be functional and non-immunogenic in man. The C-A junction was not altered and, therefore, processing of the A chain should not be altered in the transgenic fish.

EXAMPLE 4

Tilapia Insulin Promoter Analysis

As described above, the tilapia insulin gene includes approximately 1.8 Kb of 5' DNA which contains the complete insulin promoter. To test the sufficiency of this DNA to control expression, this region is ligated to a functional "reporter" gene such as beta-galactosidase, chloroamphenicol acetyl transferase (CAT), green fluorescent protein (GFP), or the like. This reporter DNA/insulin promoter construct is transfected into various cell lines (e.g., CHO, WEBHI3, and Rin cell lines). The Rin cell lines are a rat islet beta cell line and are used to determine if the tilapia insulin promoter is specific for beta cells. There are two variants of the rat Rin cells (Rin-M which secretes insulin, somatostatin, and Rin-14B which only secretes somatostatin). The functionality of the promoter is determined by transient transfection. Various DNA deletions are tested on this insulin promoter to determine which areas are required for optimal expression (including those which may be involved in tissue specificity).

Primates have a 14 bp tandem repeat minisatellite located 363 bp upstream of the translation start site in their insulin gene. This minisatellite is highly polymorphic ranging from 40 to 157 repeats. There is a high genetic susceptibility to insulin-dependent diabetes mellitus in individuals who have a short number of repeats as compared to those with longer number of tandem repeats. Interestingly, the tilapia insulin gene also contains a repetitive element near the same location (–282 bp). This repetitive element is a microsatellite with 17 repeats of "CA". The effect, if any, of this repeat on gene expression is determined by removal of the element from the gene. These tests are then repeated in vivo using the GFP constructs to determine if the promoter is specific to the Brockmann bodies. This information establishes the amount of 5' upstream sequence both necessary and sufficient for expression of invention transgenes.

The 5' flanking region contains numerous sequences that may be involved in insulin specific gene expression. Several ICE-like sequences have been given various names (e.g. RIPE, IEB1, IEB2, NIR, FAR) depending on their location, but they all contain the basic sequence CANNTG referred to as the E box. These E box sequences have been shown to bind helix-loop-helix (HLH) transcription factors. Since many of these similar control elements are located in the identical position in mammalian and tilapia insulin genes, the molecular regulation of insulin expression in fish is thought to be similar to that found in higher animals. Analysis of deletion mutations in these regions is expected to reveal a decrease in glucose sensitive regulation of insulin expression.

EXAMPLE 5

Preparation of Transgenic Fish

To create transgenic fish, the humanized or modified gene is inserted into fertilized tilapia ova. First, the modified gene insert is removed from the plasmid DNA. The DNA is suspended in NT buffer (88 mM NaCl, 10 mM Tris-HCl pH 7.5) and $10^6$–$10^7$ copies are injected into each pronucleus (Rahman, M. A. and Maclean, N., Production of Transgenic tilapia (*Oreochromis niloticus*). A linear fragment increases the likelihood of integration and also decreases the occurrence of extrachromosomal copies of the gene (Id.).

Unlike mice, which may produce 10–15 eggs at a time, fish may produce thousands of eggs at once. Tilapia are particularly prolific and are, in many ways, ideal for transgenic studies. Unlike many other teleost fish species which spawn once a year, female tilapia are ready to spawn every two weeks. Tilapia grow quickly and become sexually mature in five months.

Tilapia broodstock and offspring can be pit tagged to enable identification of individual fish by electronic scanning. Broodstock, a male and a female separated by a perforated plastic sheet, are kept in 20 gallon aquariums at 28° C. When the female becomes ripe, her eggs are stripped into a dry petri dish and the male's milt (semen) are stripped into a capillary tube. The tube's contents are mixed with the eggs and then water is added to the dish. After 2–3 minutes, the eggs are washed to remove excess sperm. Eggs are microinjected beginning within 5 minutes of fertilization. Fertilized eggs are maintained in water at 21° C, which slows down division, so that the fertilized eggs remain unicellular prior to injection. This technique has been reported to permit microinjection of tilapia eggs for up to about 2.5 hours after fertilization (Rahman, M. A. and Maclean, N., Production of Transgenic tilapia (*Oreochromis niloticus*) by one cell stage microinjection. Aquaculture 105: 219–32, 1992).

Teleost fish eggs have micropyles, a single sperm-sized opening in the chorion. The micropyle diameter of a tilapia egg is 6 $\mu$m. Micropyle injections are performed as described by Rahman and Maclean (supra). Eggs are positioned with the micropyle readily visible and then immobilized in an egg holder. With the aid of an operating microscope and a micromanipulator, the needle tip is advanced down the micropyle and 250 pl -2 nl of DNA solution injected using a "gene pusher." The needles, measuring 3–5 $\mu$m at the end, are made from borosilicate glass tubes using an microelectrode puller. Following injection, the eggs are kept in plastic hatching funnels with a water flow rate of 0.75 1/minute until 10 days post-fertilization at which time the fry are transferred to an aquarium and allowed to grow (id.).

Once introduced into tilapia by microinjection, the humanized tilapia insulin gene contains enough tilapia sequences so that homologous recombination occurs in some percentage of fish. As a confirmation, screening is performed as outlined in Example 7. Individual fish expressing the transgene are pit tagged at 3 months of age so that they can be identified through their lives by electronic scanning.

EXAMPLE 6

Embryonic Stem (ES) Cell Technology

In mice, ES-cell technology has been used extensively to produce targeted gene mutations and gene knockouts in vitro. These transfected ES cells can then be injected into developing blastulas to generate chimeras, including germ-line chimeras, and these germ-line chimeras can be used to produce homozygous knockout mice. This approach is also applicable to tilapia. It is now possible to grow zebrafish and Japanese medaka blastula cells in tissue culture and block their differentiation resulting in "ES-like" cells (Se, e.g., Hong, Y., et al., PNAS 95:3679 (1998); Lin, S., et al., PNAS, 89:4519 (1992); Sun, L., et al., Mol. Marine Biol. Biotechnol. 4:193 (1995); Ghosh, C. and Collodi, P., Cytotechol. 14:21 (1994); Speksnijder, J. E., et al., Mol. Marine Biol. Biotechnol. 6:21 (1997)). Recently, stable medaka ES cell lines were used to produce chimeras; DNA transfection was also possible in these fish ES lines (Hong, Y., supra). The technique taught for zebrafish, however, is not directly adaptable to tilapia without major modification at almost every step. For instance, the chorion surrounding the developing blastula is much thicker in tilapia embryos and is resistant to digestion with pronase (i.e., the method of freeing the blastulas in zebrafish). In zebrafish, the blastulas are harvested at 3 hours after fertilization (roughly the 1000-cell stage); tilapia are not even approaching a blastula stage at three hours.

Therefore, a study of embryonic development in tilapia was undertaken to solve some of these problems as they arise. It was found that the 1000 cell stage occurs at roughly 10 hours post fertilization in tilapia. The location of the "hatching glands" in developing tilapia embryos was also determined (tilapia embryos use a hatching enzyme to break free of their eggs at the time of hatching). The hatching glands had not previously been described in tilapia embryos. This technology enabled the development of a hatching solution which has been successfully used to de-chorionate the developing embryos to allow access to the blastulas without destroying them. Hatching solution comprises the above-referenced hatching enzyme (chlorion) isolated from a large number of hatched tilapia and concentrated in a small volume of suitable aqueous solution or water.

Using the same tissue culture conditions and growth factors as used for zebrafish and medaka, ES cell lines from tilapia are developed. These ES cells are transfected with the humanized tilapia insulin gene. Several approaches can be taken at this stage with different vectors that offer either or both positive and negative selection markers. In one scenario, the native tilapia gene is replaced with the humanized construct (i.e., homologous recombination; confirmed by PCR); in another scenario heterozygous "knockout insulin gene" tilapia strains are developed first prior to we transfection. This latter approach may be preferable since the positive selection also introduces a segment of foreign DNA which may alter the regulation of the transfected DNA. Transfected ES cells are then placed into newly developing tilapia blastocysts. By using ES cells from grey tilapia and developing blastulas from white tilapia, color differentiation can be employed to screen for chimerism (i.e., grey and white fish). Chimeric fish are then screened to determine if sperm or eggs have the altered gene. Next positive fish will be bred to homozygosity and then tested for regulatable humanized insulin production. The ES cells offer several advantages. Millions of cells can be transfected. Selectable markers offer a rapid screening for cells that take up the DNA and also for rare homologous recombination events.

EXAMPLE 7

Screening for Transgenic Fish

The breeding program is based in part on the screening with four PCR primers: e.g., primer (AT) tilapia sequence just upstream of the 1.8 kb leading strand of the insert, primer (BT) tilapia sequence in the leading strand outside the humanized coding region, primer (CH) humanized tilapia sequence in the insulin coding region, and primer (CT) tilapia sequence homologous to CH.

In another aspect of the invention, recently hatched fry are screened using an improvement on the method of whole body proteolytic digestion originally developed by Kawakami and Hopkins (Differentiation, 58:291–295, 1995); because this method was initially developed for screening zebrafish for transgene incorporation it was not directly applicable to tilapia without additional experimentation.

The improved method comprises placing hatchlings in multi-well clusters (i.e., 1 fish/well), wherein the wells contain a mild proteinase K solution (1 microgram per microlitre) and allowed to swim for about 18 minutes; the solution from each well is then aspirated and replaced with water. The proteinase K is then inactivated by boiling for a suitable time period and the solution from each individual well (containing minute amounts of fish extracted DNA) is then tested by PCR using tilapia insulin gene-specific primers and humanized tilapia insulin specific primers.

The first pair of primers indicate if a sufficient quantity of DNA was extracted for PCR while the second pair indicate the presence of the incorporated gene. While the solution from each well is tested, the fry remain segregated as individuals in the multi-well clusters. Once the PCR results are known, any positive fry can be segregated into a separate grow-out tank, while the other siblings can be pooled together in a single tank.

While adapting the above-described technique to tilapia, several hundred fry developed from eggs microinjected with the 2.7 Kb construct (described herein) were screened. Remarkably a majority of the fish survived and yielded sufficient DNA for PCR analysis. Two positives transgenics were identified. Unfortunately, one of the fish did not survive the proteinase K screening protocol; however, re-screening of the carcass confirmed that it was also a true positive. These results indicated that older fry yielded less DNA and, thus, require longer digestion (in the presence of proteinase K) and, therefore, were more prone to dying after the digestion. Histological examination of developing tilapia fry provided an explanation for this observation; tilapia hatch on day 5 and have well developed keratinized epidermis and protective mucous by day 8 after fertilization. Therefore, the optimum time to sample DNA by this method is day 6 or 7. This method allows quick identification and segregation of fish with transgene incorporation. Early screening has the additional advantage of cutting costs.

In developing the screening methods described herein, the observed insert rate was low (slightly under 1%). Initially, a linearized 2.7 Kb humanized construct that does not contain any plasmid DNA was used for microinjection. One living transgenic animal was obtained with this 2.7 Kb gene insert. To increase the length of this DNA microinjections with the 2.7 Kb insert attached to the vector DNA (3.9 Kb) were also performed. This construct was linearized and this larger fragment was microinjected. Two living transgenic animals were obtained with this construct. Plasmid DNA (especially upstream of the gene) can potentially have negative effects on transcription of the transgene in vivo. However, all three of these trangenic animals have also been verified by detecting the gene in fin clippings. Because the size of the insert (2.7 Kb) was on the lower end of the optimal size usually used in transfections (4–5 Kb) an additional 800 bp of new 5' upstream sequence was added to the construct, resulting in a 3.5 Kb humanized tilapia insulin gene for microinjection. Using this 3.5 Kb DNA fragment six living transgenic animals have obtained. Of these six, four were verified by fin clipping. The larger construct increased the percentage of fish that incorporate the gene following microinjection.

Tilapia fin clippings can then be screened using polymerase chain reaction (PCR) (Saiki R K, Gelfand D H, Stoffel S., Scharf S J, Higuchi R, Horn G T, Mullis K B, and Erlich H A: Primer-directed enzymatic amplification of DNA with a thermostable DNA polymerase. Science 239: 487–91, 1988) using primers that incorporate the human sequences and do not give a product with the fish genome.

EXAMPLE 8

Homozygous Transgenic Founder Population

The transgenic fish (generation G0) identified by initial screening for AT (tilapia sequence just upstream of the 1.8 kb leading strand of the insert) and CH (humanized tilapia sequence in the insulin coding region) primer PCR products are heterozygotes at the insulin locus and may also contain extraneous humanized inserts elsewhere in the genome. These G0 fish are bred to as many wild-type individuals as possible, to produce a population containing 50% transgenic heterozygous offspring (G1). Fish containing one copy of the transgene are selected by screening for the AT-CH PCR product. These heterozygous fish are then mated amongst themselves to produce 25% homozygous transgenic fish in generation G2. The G2 homozygotes are selected out from the 50% heterozygotes by simultaneous screening for AT-CH and AT-CT PCR products.

The resulting homozygous transgenic founder population is expanded by random mating. Sufficient offspring are then produced to allow purification and sequencing of the transgenic insulin to confirm its amino acid sequence.

EXAMPLE 9

Purified Transgenic Population

Extraneous humanized inserts (other than at the insulin locus) in the founder population are screened and culled by southern blotting restriction digests with a humanized tilapia insulin probe. This is done in the G0 and G1 generation. Rare extraneous humanized inserts can be selected out of the founder population by screening restriction digests with the humanized tilapia insulin probe, or other suitable methods. Abundant extraneous humanized inserts can be diluted out by several generations of recurrent backcross selection to the non-transgenic base population in the MGPL, followed by another round of mating to re-establish homozygosity. The transgene is backcrossed to several strains of tilapia and when extraneous inserts have been removed, the purified transgenic population is expanded by random mating.

The possibility that tissue from transgenic tilapia may ultimately be transplanted into humans sets rigid requirements for the stability and predictability of the material. The fish used for transplantation and associated support studies should be genetically uniform. It is presently undesirable to aim for an isogenic transgenic strain that is homozygous at all background (non-insulin) loci, because of the generally poor fitness and low developmental stability of highly inbred fish. Instead, the goal is an isogenic, first generation hybrid of homozygous line crosses. Such hybrids are genetically identical, heterozygous at many background loci, but homozygous for the humanized tilapia insulin gene. Sib-mating rather than gynogenesis is a presently preferred procedure for production of homozygous lines. Multiple inbred parental lines will be developed as a security measure against loss of lines through inbreeding depression during sib-mating.

EXAMPLE 10

Transgenic Transplantation Strain

Selection for fitness (growth and fecundity) in the inbred parental strains is performed by within-family selection (e.g., as described by Uraiwan S and Doyle R W: Replicate variance and the choice of selection procedure for tilapia (*Oreochromis nilotic*) stock improvement in Thailand. Aquaculture 57: 93–8, 1986 and Doyle R W and Herbinger C: The use of DNA fingerprinting for high-intensity, with-in family selection of fish breeding. 5$^{th}$ World Congress, Genetics Applied to Livestock Production. Guelph, Ontario, Canada, pp. 364–371). Selection is performed initially on the strains themselves to reduce inbreeding depression and then secondarily on their performance in the isogenic transgenic hybrid. Since selection for fitness is likely to retard the approach of background loci towards homozygosity, this process is controlled and monitored by extensive screening at microsatellite loci distributed throughout the genome. The final transgenic transplantation strain will be an isogenic hybrid. The inbred parental lines will be sufficiently viable to create no risk of die-off during long term production of this strain.

EXAMPLE 11

Genetic Identification and Security

If necessary (for example for security or proprietary reasons), the transgenic production strain may be identifiable as such, not only at the strain level but also at the chromosome level. This can be accomplished through the development of unique allele profiles at microsatellite loci on all chromosomes. If deemed necessary fish to be made available for transplantation can be made incapable of reproduction by hormonal sterilization.

EXAMPLE 12

Non-homologous Recombination

As detailed above, homologous recombination is a presently preferred means to introduce humanized tilapia insulin as described herein. However, the humanized tilapia insulin gene contains its "natural" promoter and other upstream regulatory sequences. Therefore, when integrated into another site (i.e. non-homologous recombination), it has sufficient regulatory sequences to function. Islet cells from these transgenics would produce regulatable levels of both human and fish insulin.

Fish expressing both human and fish insulin genes may also be selected for production. Islets from such fish should still regulate blood sugar levels and, therefore, be useful as islet donors. Furthermore, fish expressing both genes (or multiple copies of the humanized gene) may demonstrate enhanced growth potential and, therefore, might prove valuable for aquaculture.

EXAMPLE 13

Functional Studies

Prior to clinical use, the functional characteristics of the transgenic islets need to be characterized. This is done in vitro and in vivo. As a first step, the amino acid sequence of the secreted insulin from the transgenic islets is determined to confirm that it is humanized. The kinetics of tilapia insulin secretion by non-transgenic tilapia islets, as well as its secretagogues, are determined in vitro and compared to secretion studies using transgenic islets and a radioimmunoassay for human insulin. Because the structure of piscine insulin differs from human, porcine, bovine, and rat insulin, most antibodies produced against insulin of these species do not crossreact with an affinity sufficient for radioimmunoassay. Although a few antibodies have been raised against teleost fish insulin, the insulin of one teleost species often differs from that of other teleost species. Therefore, antibodies to purified tilapia insulin have been raised to permit insulin measurement by standard RIA methodology. (Yang, H., et al., Immunocytochemical Characterization of the Pancreatic Islet Cells of the Nile Tilapia, Gen. and Comp. Endocrinol., 114:47–56 (1999)).

To further assess the functional characteristics of islets from transgenic fish, one could evaluate the comparative effects of tilapia, humanized tilapia, and human insulin on mammalian muscles cells, one of the primary targets of insulin. IDDM adversely affects glucose transport, glycogen synthesis, glucose oxidation, and glucose transporter GLUT-4 translocation and/or activity. These problems are normalized by appropriate insulin treatment. Therefore, evaluation of the acute and chronic effects of treatment with humanized tilapia insulin on glucose transport, glucose metabolism (glycogenesis, glycolysis, and oxidation), insulin binding, and GLUT-4 translocation is undertaken. In addition, chronic studies can be performed on streptozotocin-diabetic athymic nude mice which have been made normoglycemic with BB grafts.

Transgenic islets function appropriately in a mammalian recipient. This is carried out as described in previous studies involving transplantation of non-transgenic fish islets into nude mice (Wright, J R Jr, supra; Wright, J R Jr., Polvi S. and Maclean H: Experimental transplantation using principal islets of teleost fish (Brockmann bodies): Long-term function of tilapia islet tissue in diabetic nude mice. Diabetes 41:1528–32.1992). Diabetes should be induced in recipient mice at least one week prior to transplantation with a single intravenous injection of streptozotocin (175–200 mg/kg); all recipient mice should have at least two successive non-fasting plasma glucose measurements between 350 and 500 mg/dl. For all mouse strains tested, the optimal volume of non-transgenic tilapia BB fragments to insure normoglycemia and to minimize the probability of hypoglycemia immediately post transplantation is about 0.0025 kg of donor fish body weight/gm of mouse weight (eg., a 24 gm mouse would require about 0.6 kg of donor tilapia). The total donor fish body weight can generally be provided by one large fish or multiple small fish. Tilapia weighing between 200 and 800 gms each are usually used as BB donors. Total donor fish weight is a presently preferred method for quantifying the amount of tissue required for transplantation into a particular recipient mouse as the total number of tilapia cells has a direct linear relationship with donor body weight. (Dickson, B. C., et al., Quantification of Tilapia Islets: A Direct Relationship Between Islet Cell Number and Body Mass, Transplantation Proc., 30:621–622 (1998). Similar proportionate amounts can be employed in transplanting transgenic islets into humans. Of course, those of skill in the art will recognize that each person with diabetes or impaired glucose tolerance will have individualized insulin needs that will have to be addressed in consultation with the treating physician.

At least 30 minutes before transplantation, BB fragments are removed from the incubator, switched into CMRL media containing 4.0 mg/ml D-glucose, and then returned to the incubator for 30 minutes. This step further degranulates the islets and serves to protect the recipient from acute hypoglycemia during the first 24–48 hours after transplantation (i.e, when insulin is most likely to leak out of any dead or dying cells). After this 30 minute incubation period, BB fragments are placed in complete media containing 2.5 mg/ml D-glucose and then returned to the incubator until the time they are transplanted. Immediately prior to transplantation, the BB fragments are washed in incomplete media (i.e., without fetal calf serum).

The diabetic nude mouse recipient is anesthetized with an i.p. injection of 50–55 mg/kg sodium pentobarbitol, placed on its right side and secured. The left side is shaved and then cleansed with an iodine antiseptic solution followed by alcohol. The left kidney is palpated and then delivered through a 0.75 cm subcostal incision at the costovertebral angle. The externalized kidney is secured and moistened with HEPES-HBSS. While visualized through a dissecting microscope, the renal capsule is gently lifted with jeweler's forceps and a 0.2 cm incision is made with the cutting edge of a 25 gauge needle. A "hockey stick-shaped" glass microspatula is used to separate the capsule from the surface of the kidney—thus creating a space into which the BB tissue may be transplanted. Great care must be exercised to prevent tearing of the renal capsule with the microspatula.

BB fragments are placed beneath the kidney capsule by gently lifting the capsule with curved jeweler's forceps and then pushing each fragment under the capsule with the curved glass microspatula. Alternatively, BB fragments can be injected under the kidney capsule. The surface of the kidney should be frequently moistened with HEPES-HBSS during this process. Once all of the BB fragments are under the kidney capsule, they should be distributed evenly so that large matted masses of BB tissue are avoided. The incision in the renal capsule is then sealed using a fine tip, low-temperature ophthalmic cautery (Xomed-Treace, Jacksonville, Fla.). The kidney is then returned to its normal position and the muscular layer and the skin are closed individually with 510 silk suture (Wright, J R Jr., Polvi S. and Maclean H: Experimental transplantation using principal islets of teleost fish (Brockmann bodies): Long-term function of tilapia islet tissue in diabetic nude mice. Diabetes 41:1528–32.1992; Wright J R Jr, Kearns I 1, Polvi S et al. Experimental xenotransplantation using principal islets of teleost fish (Brockmann bodies): Graft survival in selected strains of inbred mice. Transplant Proc. 1994; 26:770).

EXAMPLE 14

Transplant Assessment a. In Vivo Graft Function

Mice generally become normoglycemic (<200 mg/dl) several hours post-transplant. Recipient mice should be observed occasionally in the post-operative period for signs of hypoglycemia. During the first 24–48 hours post transplantation, insulin release is poorly regulated and mice may fall victim to hypoglycemia. Hypoglycemic mice should be treated immediately with i.p. glucose. If a sufficient volume of BB tissue has been transplanted, mice should remain normoglycemic until rejection. Mean non-fasted plasma glucose levels after transplantation of tilapia BB fragments into nude mice are in the range of 70–100 mg/dl (Wright, J R Jr., Polvi S. and Maclean H: Experimental transplantation using principal islets of teleost fish (Brockmann bodies): Long-term function of tilapia islet tissue in diabetic nude mice. Diabetes 41:1528–32.1992); however, mean plasma glucose levels tend to be somewhat lower during the first week after transplantation. BB grafts function physiologically in nude mice; long-term recipient mice have relatively normal glucose tolerance curves (Wright, J R Jr., Polvi S. and Maclean H: Experimental transplantation using principal islets of teleost fish (Brockmann bodies): Long-term function of tilapia islet tissue in diabetic nude mice. Diabetes 41:1528–32.1992). It is of interest that mean fasting plasma glucose levels (72 mg/dl) in long-term recipient mice are nearly identical to those of the donor fish (75 mg/dl) (Wright, J R Jr., Polvi S. and Maclean H: Experimental transplantation using principal islets of teleost fish (Brockmann bodies): Long-term function of tilapia islet tissue in diabetic nude mice. Diabetes 41:1528–32.1992). If non-fasting plasma glucose levels fluctuate widely, it is likely that insufficient BB tissue was transplanted (Wright J R Jr, Polvi S, Schrezenmeir J., Al-Abdullah I. Longterm function of teleost fish principal islets (Brockmann bodies) after transplantation under the renal capsule in diabetic nude mice. Transplant Proc. 1992: 24:3029–30).

b. Histology

Histological assessment is required when each recipient mouse is sacrificed. First of all, the recipient's native pancreas should be examined histologically for evidence of Beta cell regeneration; this is accomplished by staining histologic sections for insulin with aldehyde fuchsin (Culling C F A, Allison R T, Barr W T, Aldehyde fuchsin (Halmi, 1952), In: Cellular Pathology Technique $4^{th}$ ed., London: Buttherworths, 1985: 47808) or immunoperoxidase.

Next, each left kidney should be examined for graft viability and the degree of Beta cell granulation. Beta cell granulation can be examined by immunoperoxidase staining using the above-described antibody to tilapia insulin. Sections of the graft-bearing kidney should also be stained with hematoxylin and eosin.

c. Single Cell Preparations

There may be some advantage to converting the BB fragments to single cell suspensions. This is associated with an additional advantage because single cells and small cell agglomerates display a much higher surface area to volume ratio than whole BBs or BB fragments and, therefore, are less susceptible to limitations in the diffusion of oxygen and nutrients (Schrezenmeir J, Laue C h, Sternheim E T et al., Long-term function of single-cell preparations of piscine principal islets in hollow fibers. Transplant Proc. 1992; 24:2941–5).

BBs can be easily dispersed into single cells. BBs are placed in a 15 cc plastic conical centrifuge tube and washed twice with calcium-magnesium-free HBSS. The wash solution is aspirated and the BB are resuspended in 7 ml of VERSENE (Gibco #670–5040AG, Grand Island, N.Y.) and are maintained at room temperature for seven minutes. The BBs are sedimented and the supernatant removed. Next, 4 ml of a trypsin solution (Sigma #T-0646, St. Louis, Mo.; 1 mg/ml in calcium-magnesium-free HBSS filtered through a 0.22 um syringe filter) is added to the tube and the tube is then placed in a 37° C. water bath inside a laminar flow hood; the trypsin/BB solution is then gently pipetted up and down constantly. After about two minutes, the larger fragments are allowed to sink to the bottom and the supernatant containing free islet cells is removed and immediately transferred to a tube containing complete tissue culture media which is then placed on ice. An additional 4 ml of the trypsin solution is added to the pellet and this process is repeated three times. Each time the supernatant is pooled and diluted with complete media. Finally, the tube containing the supernatant is centrifuged at 600 g for 5 minutes at 4° C. The supernatant is removed and the cells are resuspended in complete tissue culture media and counted. Viability, as assessed by trypan blue exclusion, is about 95%. Compared to dispersed rodent or human islet cells, dispersed BB cells have less tendency to reaggregate into clumps or chains of cells after overnight culture, although some reaggregation will occur. Although single cell suspensions immobilized in plasma clots will produce normoglycemia when transplanted under the renal capsules of diabetic nude mice, data suggests that single cell preparations do not function in vivo quite as well as BB fragments—probably because cell-cell communications are diminished (Pipeleers D, In't Veld P, Maes E, and Van de Winkel M: Glucose-induced insulin release depends on functional cooperation between islet cells. Proc. Natl. Acad. Sci. USA 79: 7322–5, 1982).

As an alternative to single cell methods, the BBs can simply be teased apart and then cultured which will produce similar mammalian islet-sized BBs. It has previously been shown that BBs prepared in this fashion from non-transgenic tilapia can be successfully transplanted into the testes or under the kidney capsules of diabetic nude mice and will produce long-term normoglycemia.

EXAMPLE 15

Transplantation into Humans

BBs from transgenic fish of the present invention, once characterized, can be harvested, encapsulated, and surgically transplanted into diabetic patients. The BBs can be encapsulated according to known techniques in the art for encapsulating islet cells (Iwata H, Kobayashi K, Takagi T, Oka T, Yang H, and Amemiya H: Feasibility of agarose microbeads with xenogeneic islets as a bioartificial pancreas. J. Biomed. Mater, Res. 28:1003–11, 1994: Iwata H, Takagi T, Kobayashi K, Oka T, Tsuji T, and Ito F: Strategy for developing microbeads applicable to islet xenotransplantation into a spontaneous diabetic NOD mouse. J. Biomed. Materials Res, 28:1201–7, 1994; Lanza R P, Ecker D, Kuntreiber W H, Staruk J E, Marsh J, and Chick W L: A simple method for transplanting discordant islets into rats using alginate gel spheres. Transplantation 59:1485–9, 1995). It has previously been shown that macroencapsulated BBs from non-transgenic tilapia will provide long-term normoglycenia and mammalian-like glucose tolerance profiles after intraperitoneal transplantation in mice (Yang H et al., Long-term function of fish islet xenografts in mice by alginate encapsulation. Transplantation, 64:28–32 (1997)). Additional steps for reducing the immunogenicity of the transplanted BBs are known in the art and can be undertaken as needed.

One problem that has plagued investigators working with the various artificial pancreas technologies is that much of initial islet volume is lost after encapsulation because of central necrosis secondary to hypoxia in the centre of the islets. Piscine islet tissue is superior to mammalian islet tissue for encapsulation because fish tissues, including islets, can tolerate lower oxygen tensions (Wright, et al., Tilapia—A Source of Hypoxia-Resistant Islet Cells for Encapsulation, Cell Transplantation, 7:299–307 (1998)). Even if glucose-stimulated insulin secretion by the transgenic fish islets is somewhat less efficient or slightly slower than that of human islets, they are still exceedingly useful for preparation of artificial pancreases, e.g., with a large number of fish islets and a much smaller number of human islets; conceivably the fish islets could provide the bulk of the insulin production and the human islets could "fine tune" the insulin response, just as short-acting and long-acting insulins are now mixed to optimize insulin therapy in diabetics.

Transgenic fish islets described herein represent a nearly unlimited supply of human insulin-producing islet tissue that would not require expensive enzymatic islet isolation procedures for procurement. The utility of these islets is further increased in that tilapia BBs can be cryopreserved in liquid nitrogen (using standard techniques developed for cryopreserving mammalian islets), thawed, and then transplanted for confirming islet function. (O'Hali, et al., Cryopreservation of Principal Islets of Teleost Fish: The Effect on Function and Islet Xenograft Survival, Transplant. Proc., 29:1990–91 (1997)). This property facilitates shipping and long-term storage of the transgenic islets.

EXAMPLE 16

Other Applications of the Invention

As described in detail above, the transgenic fish of the present invention are useful in providing islet cells for transplantation into diabetics. Such islet cells are capable of producing large amounts of humanized insulin for the treatment of diabetes. This may occur through the homologous recombination of the humanized tilapia insulin gene. However, if non-homologous recombination occurs, the transgenic fish may express both human and fish insulin genes. These fish may be used since fish insulin is functional in humans. Such fish may also be useful in aquaculture as fish expressing both genes (or multiple copies of the human gene) are expected to demonstrate enhanced growth.

As will be recognized by those skilled in the art, the various embodiments described herein are provided by way of illustration and not limitation; various modifications and substitutions may be made thereto without departing from the spirit and scope of the invention. Such modifications and substitutions are contemplated as within the scope of the following claims.

---

That which is claimed is:

1. A transgenic Tilapia whose genome comprises a humanized insulin gene, wherein the humanized insulin gene comprises a sequence encoding a humanized insulin protein under the control of the regulatory sequences of a Tilapia insulin gene, wherein said humanized insulin protein is biologically active in humans and the islet cells of the Tilapia secrete said insulin protein.

2. An islet cell isolated from the transgenic Tilapia of claim 1, wherein the genome of said cell comprises a humanized insulin gene.

3. The transgenic Tilapia of claim 1 wherein the humanized insulin gene comprises SEQ ID NO:6.

4. The transgenic Tilapia of claim 1 wherein the humanized insulin gene comprises SEQ ID NO:7.

* * * * *

UNITED STATES PATENT AND TRADEMARK OFFICE
CERTIFICATE OF CORRECTION

PATENT NO. : 6,476,290 B1 Page 1 of 1
DATED : November 5, 2002
INVENTOR(S) : Wright and Pohajdak It is certified that error appears in the above-identified patent and that said Letters Patent is hereby corrected as shown below:

<u>Title page,</u>
Item [57], ABSTRACT,
In the second sentence, after "Humanized insulin" insert -- genes of --

Signed and Sealed this

First Day of April, 2003

JAMES E. ROGAN
*Director of the United States Patent and Trademark Office*

SEQUENCE LISTING

<160> NUMBER OF SEQ ID NOS: 16

<210> SEQ ID NO 1
<211> LENGTH: 21
<212> TYPE: PRT
<213> ORGANISM: Oreochromis niloticus

<400> SEQUENCE: 1

Gly Ile Val Glu Glu Cys Cys His Lys Pro Cys Thr Ile Phe Asp Leu
 1               5                  10                  15

Asn Gln Tyr Cys Asn
            20

<210> SEQ ID NO 2
<211> LENGTH: 30
<212> TYPE: PRT
<213> ORGANISM: Oreochromis niloticus

<400> SEQUENCE: 2

Val Gly Gly Pro Gln His Leu Cys Gly Ser His Leu Val Asp Ala Leu
 1               5                  10                  15

Tyr Leu Val Cys Gly Asp Arg Gly Phe Phe Tyr Asn Pro Arg
            20                  25                  30

<210> SEQ ID NO 3
<211> LENGTH: 21
<212> TYPE: PRT
<213> ORGANISM: Homo sapiens

<400> SEQUENCE: 3

Gly Ile Val Glu Gln Cys Cys Thr Ser Ile Cys Ser Leu Tyr Gln Leu
 1               5                  10                  15

Glu Asn Tyr Cys Asn
            20

<210> SEQ ID NO 4
<211> LENGTH: 30
<212> TYPE: PRT
<213> ORGANISM: Homo sapiens

<400> SEQUENCE: 4

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30

<210> SEQ ID NO 5
<211> LENGTH: 2078
<212> TYPE: DNA
<213> ORGANISM: Oreochromis niloticus

<400> SEQUENCE: 5
gtccccataa tcgcacacaa gtccccacaa tgtaggtgaa ataggttcca cggaaacacg      60
tggaacaggg ggtgtgtcca ggtggtgctg gtggagtata aatggagaga aggctcttgg     120
ttctgcctca cacagaaaag ctgctcctgc ccttcatctc agagttacct cctcctctct     180
gtctgtgcag gtgagtgctg gctgtaggtt tggttgtgag gacagtgact gtgatgctaa     240
cgtgaatgtg cttttgtgtt cagctctttt ccagcatggc agcgctctgg ctccaggcct     300
tctccctgct cgtcttaatg atggtttcgt ggccgggctc ccaggccgtc ggtgggccac     360
agcacctgtg cggctcccac ctggtggatg ccctgtacct ggtctgtggg acagaggct     420 tcttctacaa ccccaggaga gatgtggacc ctctgcttgg tgagaccacc aaccacaaac     480
agaaacacta gacaaactat ttgagggcag cttttctttc tctgagttca ctttaaatca     540
gctttcatgt tggaaacatg gtaatagtaa ttttccatat ctttatggac cctacatgat     600
tagtttacat ctattgccat ttgtctcaac acctgcatca tataatagcg ctgattttgt     660
aacactttgt gttagaatta gtaatttatg ttctaataat gtttgatatg tattctttaa     720
tataaatgac cagaattttt agatctgaac attcacctgc tcttcatccc atcaggtttc     780
ctccctccaa aggcaggtgg tgctgtggtg caaggtggtg agaatgaagt gaccttcaaa     840

-continued

```
gaccagatgg aaatgatggt gaagcgaggc attgtggagg aatgctgtca caaaccctgt      900
accatcttcg acctgcagaa ctactgcaac tgaactgctc tgctggactt tgtttagtcg      960
agccaggctc ggctattcag gtctgagtcc cagccccacc tcgctccctg cttcagagga     1020
gagccacagc tgtcctctct ctgaaaacca actgctgtca aatgaagtgc tgagaaatgg     1080
ataaaattaa ttttccaaga aataaaaatg caaaatgtga caacgtgagg caaaaaagtg     1140
tgttcttttg ttgtgatgaa ttcagttaat tgattaaagt gaaaactcga acatgttagg     1200
tacctgctgc tatccagcac aaactgctga gctttcactt tccaaagctt tgtgtttagc     1260
ttatagtgtc tctgaacagg atataaacac atcatgcact ctgacatgat gtccttttca     1320
aacaatccct tgtcatcttc atttcagcag gtcagtgttt tttattcagg tcctcgtgat     1380
gacacagaag ataaaaacac caagtattct aaaaattatc aaattgaatt ttaagttcaa     1440
aagcattctt ccatcacagt caacagaacc ccaagacctg aagttccaaa ggcctgtggt     1500
gttaccacta tgctatctac atatgttacc tgcttttaac tattaaacgg agcagatgga     1560
tcagaaggtt aatagctgat cagatcatgt cagctcatta gcttcagttt gttttactga     1620
gtgctgtaac cactcaatca gaaacacact gttacttaat ctgagtacat acttgtatac     1680
attaaacttg gaaaagata datgtgaaat gtaaaagtga ggtcaatcgt caaatgtgac      1740
acgatatttg gatctgttta tccttccagg atcacggggc ggggagagcc tatcccagct     1800
accatagtgc gagaggtcag gtacaccctg gagaggtcaa cagcctgtca cagggtttac     1860
gctcagagac aagcaaccac gccacttcgg cttataccag tattatttcc taaatgttgc     1920
caataaaaaa caaatcagt agaattttaa gcagttttca ttttaattta acctcatttg      1980
aagaagaagt cagaggtcca aagtatggga atatttataa ttccaatgtt gtcaattcaa     2040
ataatggcaa taagaaacat agtttgaaat agaataag                             2078
```

<210> SEQ ID NO 6
<211> LENGTH: 2070
<212> TYPE: DNA
<213> ORGANISM: Artificial Sequence
<220> FEATURE:
<223> OTHER INFORMATION: humanized tilapia insulin gene

<400> SEQUENCE: 6

```
gtccccataa tcgcacacaa gtccccacaa tgtaggtgaa ataggttcca cggaaacacg       60
tggaacaggg ggtgtgtcca ggtggtgctg gtggagtata aatggagaga aggctcttgg      120
ttctgcctca cacagaaaag ctgctcctgc ccttcatctc agagttacct cctcctctct      180
gtctgtgcag gtgagtgctg gctgtaggtt tggttgtgag gacagtgact gtgatgctaa      240
cgtgaatgtg cttttgtgtt cagctctttt ccagcatggc agcgctctgg ctccaggcct      300
tctccctgct cgtcttaatg atggtttcgt ggccgggctc ccaggccttc gtgcagcagc      360
acctgtgcgg atcccacctg gtggaggccc tgtacctggt ctgtggggag agaggcttct      420
tctacacccc caagagagat gtggaccctc tgcttggtga gaccaccaac cacaaacaga      480
aacactagac aaactatttg agggcagctt ttctttctct gagttcactt taaatcagct      540
ttcatgttgg aaacatggta atagtaattt tccatatctt tatggaccct acatgattag      600
tttacatcta ttgccatttg tctcaacacc tgcatcatat aatagcgctg attttgtaac      660
actttgtgtt agaattagta atttatgttc taataatgtt tgatatgtat tctttaatat      720
aaatgaccag aatttttaga tctgaacatt cacctgctct tcatcccatc aggtttcctc      780
cctccaaagg caggtggtgc tgtggtgcaa ggtggtgaga atgaagtgac cttcaaagac      840
```

| | |
|---|---|
| cagatggaaa tgatggtgaa gcgaggcatt gtggagcaat gctgtacctc catttgttcc | 900 |
| ctgtaccagc tggagaacta ctgcaactga actgctctgc tggactttgt ttagtcgagc | 960 |
| caggctcggc tattcaggtc tgagtcccag ccccacctcg ctccctgctt cagaggagag | 1020 |
| ccacagctgt cctctctctg aaaccaact gctgtcaaat gaagtgctga gaaatggata | 1080 |
| aaattaattt tccaagaaat aaaaatgcaa atgtgacaa cgtgaggcaa aaagtgtgt | 1140 |
| tcttttgttg tgatgaattc agttaattga ttaaagtgaa aactcgaaca tgttaggtac | 1200 |
| ctgctgctat ccagcacaaa ctgctgagct ttcactttcc aaagctttgt gtttagctta | 1260 |
| tagtgtctct gaacaggata taaacacatc atgcactctg acatgatgtc cttttcaaac | 1320 |
| aatcccttgt catcttcatt tcagcaggtc agtgtttttt attcaggtcc tcgtgatgac | 1380 |
| acagaagata aaacaccaa gtattctaaa aattatcaaa ttgaatttta agttcaaaag | 1440 |
| cattcttcca tcacagtcaa cagaaccca agacctgaag ttccaaaggc ctgtggtgtt | 1500 |
| accactatgc tatctacata tgttacctgc ttttaactat taaacggagc agatggatca | 1560 |
| gaaggttaat agctgatcag atcatgtcag ctcattagct tcagtttgtt ttactgagtg | 1620 |
| ctgtaaccac tcaatcagaa acacactgtt acttaatctg agtacatact tgtatacatt | 1680 |
| aaacttggaa aaagatagat gtgaaatgta aagtgaggt caatcgtcaa atgtgacacg | 1740 |
| atatttggat ctgtttatcc ttccaggatc acggggcggg gagagcctat cccagctacc | 1800 |
| atagtgcgag aggtcaggta cacctggac aggtcaacag cctgtcacag ggtttacgct | 1860 |
| cagagacaag caaccacgcc acttcggctt ataccagtat tatttcctaa atgttgccaa | 1920 |
| taaaaaacaa aatcagtaga attttaagca gttttcattt taatttaacc tcatttgaag | 1980 |
| aagaagtcag aggtccaaag tatgggaata tttataattc caatgttgtc aattcaaata | 2040 |
| atggcaataa gaaacatagt ttgaaataga | 2070 |

<210> SEQ ID NO 7
<211> LENGTH: 2075
<212> TYPE: DNA
<213> ORGANISM: Artificial Sequence
<220> FEATURE:
<223> OTHER INFORMATION: humanized tilapia insulin gene

<400> SEQUENCE: 7

| | |
|---|---|
| gtccccataa tcgcacacaa gtccccacaa tgtaggtgaa ataggttcca cggaaacacg | 60 |
| tggaacaggg ggtgtgtcca ggtggtgctg gtggagtata aatggagaga aggctcttgg | 120 |
| ttctgcctca cacagaaaag ctgctcctgc ccttcatctc agagttacct cctcctctct | 180 |
| gtctgtgcag gtgagtgctg gctgtaggtt tggttgtgag acagtgact gtgatgctaa | 240 |
| cgtgaatgtg cttttgtgtt cagctctttt ccagcatggc agcgctctgg ctccaggcct | 300 |
| tctccctgct cgtcttaatg atggtttcgt ggccgggctc ccaggccttc gtgcagcagc | 360 |
| acctgtgcgg atcccacctg gtggaggccc tgtacctggt ctgtggggag agaggcttct | 420 |
| tctacacccc caagaccaga gatgtggacc ctctgcttgg tgagaccacc aaccacaaac | 480 |
| agaaacacta gacaaactat ttgagggcag cttttcttc tctgagttca ctttaaatca | 540 |
| gctttcatgt tggaaacatg gtaatagtaa ttttccatat ctttatggac cctacatgat | 600 |
| tagtttacat ctattgccat ttgtctcaac acctgcatca tataatagcg ctgattttgt | 660 |
| aacactttgt gttagaatta gtaatttatg ttctaataat gtttgatatg tattctttaa | 720 |
| tataaatgac cagaattttt agatctgaac attcacctgc tcttcatccc atcaggtttc | 780 |

-continued

```
ctccctccaa aggcaggtgg tgctgtggtg caaggtggtg agaatgaagt gaccttcaaa      840
gaccagatgg aaatgatggt gaagcgaggc attgtggagc aatgctgtac ctccatttgt      900
tccctgtacc agctggagaa ctactgcaac tgaactgctc tgctggactt tgtttagtcg      960
agccaggctc ggctattcag gtctgagtcc cagccccacc tcgctccctg cttcagagga     1020
gagccacagc tgtcctctct ctgaaaacca actgctgtca aatgaagtgc tgagaaatgg     1080
ataaaattaa ttttccaaga aataaaaatg caaaatgtga caacgtgagg caaaaaagtg     1140
tgttcttttg ttgtgatgaa ttcagttaat tgattaaagt gaaaactcga acatgttagg     1200
tacctgctgc tatccagcac aaactgctga gctttcactt tccaaagctt tgtgtttagc     1260
ttatagtgtc tctgaacagg atataaacac atcatgcact ctgacatgat ctccttttca     1320
aacaatccct tgtcatcttc atttcagcag gtcagtgttt tttattcagg tcctcgtgat     1380
gacacagaag ataaaaacac caagtattct aaaaattatc aaattgaatt ttaagttcaa     1440
aagcattctt ccatcacagt caacagaacc ccaagacctg aagttccaaa ggcctgtggt     1500
gttaccacta tgctatctac atatgttacc tgcttttaac tattaaacgg agcagatgga     1560
tcagaaggtt aatagctgat cagatcatgt cagctcatta gcttcagttt gttttactga     1620
gtgctgtaac cactcaatca gaaacacact cttacttaat ctgagtacat acttgtatac     1680
attaaacttg gaaaagata  gatgtgaaat gtaaagtga  ggtcaatcgt caaatgtgac     1740
acgatatttg gatctgttta tccttccagg atcacggggc ggggagagcc tatcccagct     1800
accatagtgc gagaggtcag gtacaccctg gacaggtcaa cagcctgtca cagggtttac     1860
gctcagagac aagcaaccac gccacttcgg cttataccag tattatttcc taaatgttgc     1920
caataaaaaa caaaatcagt agaattttaa gcagttttca ttttaattta acctcatttg     1980
aagaagaagt cagaggtcca agtatggga  atatttataa ttccaatgtt gtcaattcaa     2040
ataatggcaa taagaaacat agtttgaaat agaat                                 2075
```

<210> SEQ ID NO 8
<211> LENGTH: 8
<212> TYPE: PRT
<213> ORGANISM: Lophius americanus

<400> SEQUENCE: 8

Tyr Asn Pro Lys Arg Asp Val Asp
1               5

<210> SEQ ID NO 9
<211> LENGTH: 8
<212> TYPE: PRT
<213> ORGANISM: Oreochromis niloticus

<400> SEQUENCE: 9

Tyr Asn Pro Arg Arg Asp Val Asp
1               5

<210> SEQ ID NO 10
<211> LENGTH: 12
<212> TYPE: PRT
<213> ORGANISM: Homo sapiens

<400> SEQUENCE: 10

Tyr Thr Pro Lys Thr Arg Arg Glu Ala Glu Asp Leu
1               5                   10

<210> SEQ ID NO 11

-continued

```
<211> LENGTH: 21
<212> TYPE: DNA
<213> ORGANISM: Artificial Sequence
<220> FEATURE:
<223> OTHER INFORMATION: IN-6 reverse primer

<400> SEQUENCE: 11
tgtagaagaa gcctctgtcc c                                         21

<210> SEQ ID NO 12
<211> LENGTH: 1725
<212> TYPE: DNA
<213> ORGANISM: Oreochromis niloticus

<400> SEQUENCE: 12
gaatttacat cgattgtgca gttttgacag aaaatgtttt tatagtttga ttgtggggtg      60
acagcggctc tggtttctgg ttcattggtg gagcagatgc agatgagaaa acacaaagtt     120
gtctgaaaca cgcgtcctcc ttcgtcatgg acagctcgtc atggtaacgc tctttctcgg     180
tcagttgtgc agcttcttta agagactaac aagctggaac aagagctctg tcagcacacc     240
tctgacaccc attaagcact ctttggatgg cagatggttt gatgaggctc tgggttttg      300 tgcagtcggg ctcttcctca ctgcgtgact gaaaaaatac aaacttgaac tagagctgaa     360
gtcatcttag acccataact acaataaact atttgtaaca tcaggacagt caagcttttg     420
tctttgtgtt tcatgctgtc tgcgtagttc agggttgtca acatcaggc ccgggggccg      480 agaaattggc caccaaagac tctaagccac ctcattgaat gactttgaac aatgtgatga     540
agggcatgag ttttaaactt catattcatg agtttacag ttttcccagc tgataaagaa      600
ctcgcctgta agtaagtaat aaaaaaaaaa ccaatgtgca tatgaaatag atcttttata    660
caatctgtcc acattaaaaa aaataaataa ataaataaat ctgaaatttt cttttatta     720 acaaaaattt cagtttata actacaggac attttagcag ttttttttct actgaaattg     780
tgcttttttc agatcttctt tttccttttt tctgatcttc tgagctctgt caggaattac     840
atgtgtaatt aaacttcttt acagttacac gactgagttt gaaatacttt gaaatacttt    900
gaaatcttct gacatgtttc gcttcactct gagctctgct gcacatcctg atttcttttt    960
acaaacgttc agtcacacat ttcatcacaa atatcagctc tttgacgaaa agacagcttg    1020
gacttatttt catgtctgtt aacgtcaggc gtgatggagg ataggagatg ctgcattatg    1080
tgaacacatc ttgtaaaaaa gctgaataaa atgatttct acgactgtta tctgcttta      1140 actaatgagc tgagcagatg gagcagaagg ttaatagctg atcagatcat gtcggctcat    1200
tagcttcagt ttgttttact aagtgctgta accagtcaat cagaaacaca ctggcactta    1260
atatgtgctg atggcagcgc atctgtttgt ccacacacac acacacacac acacacacac    1320
acacagattc gtctcgccat ctcttcacag ggctgttcat tgactaacgt tcaatttctg    1380
aaagttaaac caaatctttc acctcaggtt taataaatca tattaagggt attttgcag     1440 agtccccata atccgtaatc gcacacaagt ccccacaatg taggtgaaat aggttccacg    1500
gaaacacgtg aacaggggg tgtgtcaggt ggtgctggtg gagtataaat ggagagaagg     1560
ctcttggttc tgcctcacac agcccagctg ctcctgccct tcatctcaga gttacctcct    1620
cctctctgtc tgtgcaggtg agtgctggct gtaggtttgg ttgtgaggac agtgactgtg    1680
atgctaacgt gaatgtgctt ttgtgttcag ctcttttcca gcatg                    1725

<210> SEQ ID NO 13
<211> LENGTH: 1725
```

```
<212> TYPE: DNA
<213> ORGANISM: Oreochromis niloticus
<220> FEATURE:
<221> NAME/KEY: misc_feature
<222> LOCATION: (0)...(0)
<223> OTHER INFORMATION: complementary sequence of SEQ ID NO: 12

<400> SEQUENCE: 13
catgctggaa aagagctgaa cacaaaagca cattcacgtt agcatcacag tcactgtcct      60
cacaaccaaa cctacagcca gcactcacct gcacagacag agaggaggag gtaactctga     120
gatgaagggc aggagcagct gggctgtgtg aggcagaacc aagagccttc tctccattta     180
tactccacca gcaccacctg acacaccccc tgttccacgt gtttccgtgg aacctatttc     240
acctacattg tggggacttg tgtgcgatta cggattatgg ggactctgca aaatacccct     300
taatatgatt tattaaacct gaggtgaaag atttggttta actttcagaa attgaacgtt     360
agtcaatgaa cagccctgtg aagagatggc gagacgaatc tgtgtgtgtg tgtgtgtgtg     420
tgtgtgtgtg tgtggacaaa cagatgcgct gccatcagca catattaagt gccagtgtgt     480
ttctgattga ctggttacag cacttagtaa acaaactga agctaatgag ccgacatgat      540
ctgatcagct attaaccttc tgctccatct gctcagctca ttagtttaaa gcagataaca     600
gtcgtagaaa tcattttat tcagcttttt tacaagatgt gttcacataa tgcagcatct     660
cctatcctcc atcacgcctg acgttaacag acatgaaaat aagtccaagc tgtcttttcg     720
tcaaagagct gatatttgtg atgaaatgtg tgactaacg tttgtaaaaa gaatcagga      780
tgtgcagcag agctcagagt gaagcgaaac atgtcagaag atttcaaagt atttcaaagt     840
atttcaaact cagtcgtgta actgtaaaga agtttaatta cacatgtaat tcctgacaga     900
gctcagaaga tcagaaaaaa ggaaaaagaa gatctgaaaa aagcacaatt tcagtagaaa     960
aaaaactgct aaaatgtcct gtagttataa aactgaaatt tttgttaata aaagaaaat    1020
ttcagattta ttatttatt tatttttttt aatgtggaca gattgtataa aagatctatt    1080
tcatatgcac attggttttt tttttattac ttacttacag gcgagttctt tatcagctgg    1140
aaaactgta aaactcatga atatgaagtt taaaactcat gcccttcatc acattgttca    1200
aagtcattca atgaggtggc ttagagtctt tggtggccaa tttctcggcc cccgggcctg    1260
atgtttgaca accctgaact acgcagacag catgaaacac aaagacaaaa gcttgactgt    1320
cctgatgtta caaatagttt attgtagtta tgggtctaag atgacttcag ctctagttca    1380
agtttgtatt ttttcagtca cgcagtgaga aagagcccga ctgcacaaaa acccagagcc    1440
tcatcaaacc atctgccatc caaagagtgc ttaatgggtg tcagaggtgt gctgacagag    1500
ctcttgttcc agcttgttag tctcttaaag aagctgcaca actgaccgag aaagagcgtt    1560
accatgacga gctgtccatg acgaaggagg acgcgtgttt cagacaactt tgtgttttct    1620
catctgcatc tgctccacca atgaaccaga accagagcc gctgtcaccc cacaatcaaa    1680
ctataaaaac attttctgtc aaaactgcac aatcgatgta aattc                     1725

<210> SEQ ID NO 14
<211> LENGTH: 113
<212> TYPE: PRT
<213> ORGANISM: Oreochromis niloticus

<400> SEQUENCE: 14

Met Ala Ala Leu Trp Leu Gln Ala Phe Ser Leu Leu Val Leu Met Met
  1               5                  10                  15
Val Ser Trp Pro Gly Ser Gln Ala Val Gly Gly Pro Gln His Leu Cys
```

-continued

```
                20                  25                  30
Gly Ser His Leu Val Asp Ala Leu Tyr Leu Val Cys Gly Asp Arg Gly
            35                  40                  45

Phe Phe Tyr Asn Pro Arg Arg Asp Val Asp Pro Leu Leu Gly Phe Leu
     50                  55                  60

Pro Pro Lys Ala Gly Gly Ala Val Val Gln Gly Gly Glu Asn Glu Val
 65                  70                  75                  80

Thr Phe Lys Asp Gln Met Glu Met Met Val Lys Arg Gly Ile Val Glu
                85                  90                  95

Glu Cys Cys His Lys Pro Cys Thr Ile Phe Asp Leu Gln Asn Tyr Cys
                100                 105                 110

Asn

<210> SEQ ID NO 15
<211> LENGTH: 112
<212> TYPE: PRT
<213> ORGANISM: Artificial Sequence
<220> FEATURE:
<223> OTHER INFORMATION: humanized tilapia insulin gene

<400> SEQUENCE: 15

Met Ala Ala Leu Trp Leu Gln Ala Phe Ser Leu Leu Val Leu Met Met
 1               5                  10                  15

Val Ser Trp Pro Gly Ser Gln Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Arg Asp Val Asp Pro Leu Leu Gly Phe Leu Pro
     50                  55                  60

Pro Lys Ala Gly Gly Ala Val Val Gln Gly Gly Glu Asn Glu Val Thr
 65                  70                  75                  80

Phe Lys Asp Gln Met Glu Met Met Val Lys Arg Gly Ile Val Glu Gln
                85                  90                  95

Cys Cys Thr Ser Ile Cys Ser Leu Tyr Gln Leu Glu Asn Tyr Cys Asn
                100                 105                 110

<210> SEQ ID NO 16
<211> LENGTH: 113
<212> TYPE: PRT
<213> ORGANISM: Artificial Sequence
<220> FEATURE:
<223> OTHER INFORMATION: humanized tilapia insulin gene

<400> SEQUENCE: 16

Met Ala Ala Leu Trp Leu Gln Ala Phe Ser Leu Leu Val Leu Met Met
 1               5                  10                  15

Val Ser Trp Pro Gly Ser Gln Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Asp Val Asp Pro Leu Leu Gly Phe Leu
     50                  55                  60

Pro Pro Lys Ala Gly Gly Ala Val Val Gln Gly Gly Glu Asn Glu Val
 65                  70                  75                  80

Thr Phe Lys Asp Gln Met Glu Met Met Val Lys Arg Gly Ile Val Glu
                85                  90                  95
```

```
                                          -continued

Gln Cys Cys Thr Ser Ile Cys Ser Leu Tyr Gln Leu Glu Asn Tyr Cys
            100                 105                 110
Asn
```